(12) United States Patent
Friis et al.

(10) Patent No.: US 10,960,218 B2
(45) Date of Patent: Mar. 30, 2021

(54) STACKED PIEZOELECTRIC COMPOSITES AND METHODS OF MAKING

(71) Applicant: University of Kansas, Lawrence, KS (US)

(72) Inventors: Elizabeth Annamaria Friis, Lawrence, KS (US); John Patrick Domann, Blacksburg, VA (US); Paul M. Arnold, Kansas City, KS (US)

(73) Assignee: UNIVERSITY OF KANSAS, Lawrence, KS (US)

( * ) Notice: Subject to any disclaimer, the term of this patent is extended or adjusted under 35 U.S.C. 154(b) by 149 days.

(21) Appl. No.: 15/766,535

(22) PCT Filed: Oct. 5, 2016

(86) PCT No.: PCT/US2016/055406
§ 371 (c)(1),
(2) Date: Apr. 6, 2018

(87) PCT Pub. No.: WO2017/062399
PCT Pub. Date: Apr. 13, 2017

(65) Prior Publication Data
US 2018/0296843 A1 Oct. 18, 2018

Related U.S. Application Data

(60) Provisional application No. 62/237,779, filed on Oct. 6, 2015.

(51) Int. Cl.
*A61N 1/378* (2006.01)
*H01L 41/04* (2006.01)
(Continued)

(52) U.S. Cl.
CPC ............ *A61N 1/378* (2013.01); *A61F 2/4455* (2013.01); *A61N 1/20* (2013.01); *A61N 1/3785* (2013.01);
(Continued)

(58) Field of Classification Search
CPC .... A61N 1/378; A61N 1/0551; A61N 1/3785; A61N 1/20; A61N 1/205; A61N 1/0529;
(Continued)

(56) References Cited

U.S. PATENT DOCUMENTS 6,143,035 A    11/2000  McDowell
9,082,979 B2 *  7/2015  Malek ................ F02M 51/0603
(Continued)

OTHER PUBLICATIONS

Brighton CT, Friedenberg ZB, Black J, Esterhai JL, Mitchell JEI, and Montique F 1981 Electrically Induced Osteogenesis: Relationship between Charge, Current Density, and the Amount of Bone Formed: Introduction of a New Cathode Concept Clin Orthop and Rel Res 161 pp. 121-134.
(Continued)

*Primary Examiner* — Mark Bockelman
(74) *Attorney, Agent, or Firm* — Medier Ferro Woodhouse & Mills PLLC

(57) ABSTRACT

The present application relates to stacked piezoelectric composites comprising piezoelectric structures. Suitably, the composites are useful as tissue-stimulating implants, including spinal fusion implants. The present application also relates to methods of making stacked piezoelectric composites.

12 Claims, 18 Drawing Sheets

(51) Int. Cl.

| | |
|---|---|
| H01L 41/047 | (2006.01) |
| H01L 41/053 | (2006.01) |
| H01L 41/083 | (2006.01) |
| H01L 41/18 | (2006.01) |
| H01L 41/23 | (2013.01) |
| H01L 41/277 | (2013.01) |
| H01L 41/37 | (2013.01) |
| A61N 1/20 | (2006.01) |
| H02N 2/18 | (2006.01) |
| H01L 41/113 | (2006.01) |
| A61F 2/44 | (2006.01) |
| A61N 1/05 | (2006.01) |
| A61N 1/32 | (2006.01) |
| A61F 2/28 | (2006.01) |

(52) U.S. Cl.
CPC ........ *H01L 41/042* (2013.01); *H01L 41/0475* (2013.01); *H01L 41/053* (2013.01); *H01L 41/083* (2013.01); *H01L 41/0835* (2013.01); *H01L 41/0836* (2013.01); *H01L 41/113* (2013.01); *H01L 41/183* (2013.01); *H01L 41/23* (2013.01); *H01L 41/277* (2013.01); *H01L 41/37* (2013.01); *H02N 2/181* (2013.01); *A61F 2002/2821* (2013.01); *A61N 1/056* (2013.01); *A61N 1/0529* (2013.01); *A61N 1/0551* (2013.01); *A61N 1/205* (2013.01); *A61N 1/326* (2013.01)

(58) Field of Classification Search
CPC ...... A61N 1/326; A61N 1/056; H01L 41/083; H01L 41/0835; H01L 41/113; H01L 41/0475; H01L 41/053; H01L 41/23; H01L 41/277; H01L 41/37; H01L 41/0836; H01L 41/183; H01L 41/042; H02N 2/181; A61F 2002/2821; A61F 2/4455
See application file for complete search history.

(56) References Cited

U.S. PATENT DOCUMENTS

| | | | | |
|---|---|---|---|---|
| 2013/0172662 | A1* | 7/2013 | Menzl | H04R 25/606 600/25 |
| 2015/0134061 | A1* | 5/2015 | Friis | B29C 43/003 623/17.11 |

OTHER PUBLICATIONS

Gittens RA, Olivares-Navarrete R, Rettew R, Butera RJ, Alamgir FM, Boyan BO, and Schwartz Z 2013 Electrical Polarization of Titanium Surfaces for the Enhancement of Osteoblast Differentiation Bioelectromagnetics 34 pp. 599-612.

Fredericks DC, Smucker J, Petersen EB, Bobst JA, Gan JC, Simon BJ and Glazer P 2007 Effects of direct current electrical stimulation on gene expression of osteopromotive factors in a posterolateral spinal fusion model Spine 32(2) pp. 174-181.

Sakai T, Hoshia S, and Nakamachi E 2006 Biochemical compatibility of PZT piezoelectric ceramics covered with titanium thin film J Optoelectronics and Advanced Materials 8(4) pp. 1435-1437.

Nguyen TD, Deshmukh N, Nagarah JM, Kramer T, Purohit PK, Berry MJ, and McAlpine MC 2012 Piezoelectric nanoribbons for monitoring cellular deformations Nature Nanotechnology 7 pp. 587-593.

Kettler A, Liakos L, Haegele B and Wilke HJ 2007 Are the spines of calf, pig and sheep suitable models for pre-clinical implant tests? Eur Spine J 16 pp. 2186-2192.

Smit TH 2002 The use of a quadruped as an in vivo model for the study of the spine—biomechanical considerations Eur Spine J 11 pp. 137-144.

Reitmaier S, Schmidt H, Ihler R, Kocak T, Graf N, Ignatius A and Wilke HJ 2013 Preliminary Investigations on Intradiscal Pressures during Daily Activities: An in Vivo Study Using the Merino Sheep PLoS ONE 8(7) e69610.

Burny et al., Electrical Stimulation of Bone Growth and Repair, Springer Science & Business Media, 2 pages (2012).

Morse, et al., "Mechanical Load Increases in Bone Formation via a Sclerostin-Independent Pathway," Journal of Bone and Mineral Research: The Official Journal of the American Society for Bone and Mineral Research, 29(11), 2456-2467 (2014).

Cejka D, et al. "Renal Elimination of Sclerostin Increases With Declining Kidney Function," Clin. Endocrinol. Metab., 99 (1):248-255 (2014).

Andersson GB. Epidemiological features of chronic low-back pain. Lancet 1999;354(9178):581-5.

Toth JM, Seim HB, 3rd, Schwardt JD, Humphrey WB, Wallskog JA, Turner AS. Direct current electrical stimulation increases the fusion rate of spinal fusion cages. Spine (Phila Pa 1976) 2000;25(20):2580-7.

Cook SD, Patron LP, Christakis PM, Bailey KJ, Banta C, Glazer PA. Direct current stimulation of titanium interbody fusion devices in primates. Spine J 2004;4(3):300-11.

Kane WJ. Direct current electrical bone growth stimulation for spinal fusion. Spine (Phila Pa 1976) 1988;13(3)363-5.

Kucharzyk OW. A controlled prospective outcome study of implantable electrical stimulation with spinal instrumentation in a high-risk spinal fusion population. Spine(Phila Pa 1976) I 999;24(5):465-9.

Meril AJ. Direct current stimulation of allograft in anterior and posterior lumbar interbody fusions. Spine (Phila Pa 1976) 1994; 19(21 ):2393-8.

Epstein NE. Pros, cons, and costs of INFUSE in spinal surgery. Surg Neurol Int2011;2:10.

Epstein NE, Schwall GS. Costs and frequency of "off-label" use of INFUSE for spinal fusions at one institution in 2010. Surgical neurology international 2011;2.

Carragee EJ, Hurwitz EL, Weiner BK. A critical review of recombinant human bone morphogenetic protein-2 trials in spinal surgery: emerging safety concerns and lessons learned. Spine J 2011;11(6):471-91.

Mooney V. A randomized double-blind prospective study of the efficacy of pulsed electromagnetic fields for interbody lumbar fusions. Spine 1990; 15(7):708-712.

Kahanovitz N. Electrical stimulation of spinal fusion: a scientific and clinical update. Spine J 2002;2(2):145-50.

An HS, Lynch K, Toth J. Prospective comparison of autograft vs. allograft for adult posterolateral lumbar spine fusion: differences among freeze-dried, frozen, and mixed grafts. Journal of Spinal Disorders & Techniques 1995;8(2): 131-135.

Glazer PA, Glazer LC. Electricity: the history and science of bone growth stimulation for spinal fusion. Orthop J Harvard Med School Online 2002;4:63-67.

Tobaben NE, Domann JP, Arnold PM, Friis EA. Theoretical model of a piezoelectric composite spinal fusion interbody implant. J Biomed Mater Res A 2014; 102( 4):975-81.

Biomet. Implantable spinal fusion simulators physician's manual & full prescribing information SpF PLUS-Mini, SpF-XL lib.http://www.biomet.com/spine/products.cfm?pdid=3&majcid=61; 2014.

Shenck NS, Paradiso JA. Energy scavenging with shoe-mounted piezoelectrics. IEEE Micro 2001 ;21 :30-42.

Platt SR, Farritor S, Haider H. On low-frequency electric power generation with PZT ceramics. Mechatronics, IEEE/ASME Transactions on 2005;10(2):240-252.

Krijnen MR, Mullender MG, Smit TH, Everts V, Wuisman PI. Radiographic, histologic, and chemical evaluation ofbioresorbable 70/30 poly-L-lactide-CO-D, L-lactide interbody fusion cages in a goat model. Spine (Phila Pa 1976) 2006;31(14): 1559-67.

Smit TH, Krijnen MR, van Dijk M, Wuisman PI. Application ofpolylactides in spinal cages: studies in a goat model. J Mater Sci Mater Med 2006;17(12):1237-44.

(56) References Cited

OTHER PUBLICATIONS

ASM International. Materials and Coatings for Medical Devices: Cardiovascular; 2009.
ET Incorporated. EPO-TEK 301 Technical Data Sheet. 2012.
QEP Products. Quadrant EPP Ketron 1000 PEEK Polyetheretherketone, unfilled, extruded (ASTM Product Data Sheet).
Smart Materials Corporation, 5Al, 5H2 Typical Material Properties; 2014.
SM Corporation. Typical PZT Fiber ordering and availability data. 2014.
Pachi A, Ji T. Frequency and velocity of people walking. Structural Engineer 2005;83(3).
Eichhrn C, Goldschmidtboeing F, Woias P. Bidirectional frequency tuning of a piezoelectric energy converter based on a cantilever beam. Journal of Micromechanics and Microengineering 2009; 19(9):094006.
Hu Y, Xue H, Hu H. A piezoelectric power harvester with adjustable frequency through axial pre loads. Smart materials and structures 2007; 16( 5): 1961.
Cromwell R, Schultz AB, Beck R, Warwick D. Loads on the lumbar trunk during level walking. J Orthop Res 1989;7 (3):371-7.
Saha S, Williams PA. Electric and dielectric properties of wet human cortical bone as a function of frequency. Biomedical Engineering, IEEE Transactions on 1992;39(12):1298-1304.
"2009 Spinal Fusion Surgery Worth the Cost for Stenosis Patients" Spine-Healthhttp://www.spine-health.com/blog/spinal-fusion-surgery-worth-cost-stenosis-patients.
Gan JC and Glazer PA 2006 Electrical stimulation therapies for spinal fusions: current concepts European Spine Journal 15(9) pp. 1301-1311.
Simon J and Simon B 2008 Electrical bone stimulation Musculo-skeletal Tissue Regeneration Springer pp. 259-287.
Gautschi O P, Frey S P and Zellweger R 2007 Bone morphogenetic proteins in clinical applications ANZ Journal of Surgery 77(8) pp. 626-631.
Burkus J K, Gomet MF, Dickman CA, and Zdeblick TA 2002 Anterior lumbar interbody fusion using rhBMP-2 with tapered interbody cages Journal of Spinal Disorders & Techniques 15(5) pp. 337-349.
Haid RW, Branch CL, Alexander JT and Burkus JK 2004 Posterior lumbar interbody fusion using recombinant human bone morphogenetic protein type 2 with cylindrical interbody cages The Spine Journal 4(5) pp. 527-538.
Shellock FG, Hatfield M, Simon BJ, Block S, Wamboldt J, Starewicz PM and Punchard WF 2000 Implantable spinal fusion stimulator: assessment of MR safety and artifacts Journal of Magnetic Resonance Imaging 12(2) pp. 214-223.
Cadei A, Dionisi A, Sardini E and Serpelloni M 2014 Kinetic and thermal energy harvesters for implantable medical devices and biomedical autonomous sensors Meas. Sci. Technol. 25 012003.
Pozzi M, Aung MSH, Zhu M, Jones RK and Goulermas JV 2012 The pizzicato knee-joint energy harvester: characterization with biomechanical data and the effect of backpack load Smart Mater. Struct. 21 075023.
Anton SR and Sodano HA 2006 A review of power harvesting using piezoelectric materials (2003-2006) Smart Mater. Struct. 16 RI-R21.
Walpole SC, Prieto-Merino D, Edwards P, Cleland J, Stevens G and Roberts I 2012 The weight of nations: an estimation of adult human biomass BMC Public Health 12(1) p. 439.
Kumar N, Judith MR, Kumar A, Mishra V and Robert MC 2005 Analysis of stress distribution in lumbar interbody fusion Spine 30(15) pp. 1731-1735.
Pogany G 1969 The P-relaxation in epoxy resins; the temperature and time-dependence of cure J of Materials Science 4(5) pp. 405-409.
Jeong U, Ryu D, Kim J, Kim D, Russell TP and Hawker CJ 2003 Volume contractions induced by crosslinking: a novel route to nanoporous polymer films Advanced Materials 15(15} pp. 1247-1250.
Flyer MW 2009 Stress analysis of fiber-reinforced composite materials DEStech Publications, Inc. pp. 4-6.
Goetzinger NC 2014 The Influence of Stacked Generators on Source Impedance of a Piezoelectric Spinal Fusion Implant MS Thesis University of Kansas.
Bodhak S, Bose S, Kinsel WC, and Bandyopadhyay A 2012 Investigation of in vitro bone cell adhesion and proliferation on Ti using direct current stimulation Materials Science and Engineering C 32 pp. 2163-2168.

\* cited by examiner

STACKED PIEZOELECTRIC COMPOSITES AND METHODS OF MAKING

BACKGROUND OF THE INVENTION

Field of the Invention

The present application relates to stacked piezoelectric composites comprising piezoelectric structures. Suitably, the composites are useful as tissue-stimulating implants, including spinal fusion implants. The present application also relates to methods of making stacked piezoelectric composites.

Background of the Invention

Electrical stimulation has proven to be an effective therapy to increase the success rate of spinal fusions, especially in the difficult-to-fuse population. However, in its current form, it is hampered by limitations such as the need for a battery pack or a separate implantable device to provide power, and reliance on user compliance for externally worn devices. An alternative treatment to aid in bone growth stimulation involves the use of growth factors such as bone morphogenic protein (BMP). However, studies on synthetic BMP have shown that it has a substantial risk for complication, including ectopic bone formation. The growth of bone spurs near the spinal canal is also of concern for anyone receiving this treatment. Some studies also suggest a carcinogenic effect related to the use of BMP.

One potential method by which electrical stimulation can be generated is through the use of piezoelectric materials. Piezoelectric materials are a class of ferroelectrics characterized by a net polarization, often due to a non-centrosymmetric crystalline structure. As a result, piezoelectric materials respond to stress with the generation of a net surface charge. Conversely, piezoelectric materials can be strained with the application of an electric field. Similar to high performance dielectric materials, piezoceramics are the most often used piezoelectric material, though they tend to be stiff and brittle.

Electrical stimulators either use direct current (DC) run through electrodes or generate electric and/or electromagnetic fields to provide increased bone healing; they can be used both internally and externally. Although non-invasive, external electrical stimulators have user compliance issues as patients are required to wear the devices for a given number of hours each day. Battery-operated DC electrical internal stimulators require a second surgery site for the battery, have limited lifetime, and must often be removed in another surgery.

SUMMARY OF PREFERRED EMBODIMENTS

To improve upon existing therapies, there is a need for a device that can deliver direct current (DC) stimulation to a metal electrode at the interbody space without the use of a battery pack. The present application fulfills this need.

The present application provides piezoelectric composites comprising two or more layers. Each layer suitably comprises a polymer matrix and a plurality of piezoelectric structures within the polymer matrix, wherein the layers are substantially adjacent to each other in a stacked configuration and layers are mechanically in series and electrically in parallel.

In embodiments, the polymer matrix comprises a thermoset polymer, copolymer and/or monomer, a thermoplastic polymer, copolymer and/or monomer or a thermoset/thermoplastic polymer or copolymer blend. Exemplary polymers include, but are not limited to, an epoxy or a poly(ether ether ketone).

Suitably, the piezoelectric structures comprise piezoelectric fibers or piezoelectric particles. In embodiments, the piezoelectric structures comprise lead zirconium titanate or barium titanate.

In further embodiments, the piezoelectric composites can also comprise an electrically insulating encapsulation coating surrounding an exterior of the piezoelectric composite.

Also provided are tissue-stimulating piezoelectric composites comprising two or more layers, each layer comprising a polymer matrix, and a plurality of piezoelectric structures within the polymer matrix, wherein the layers are substantially adjacent to each other in a stacked configuration. Exemplary polymers and piezoelectric structures are described herein.

In suitable embodiments, the piezoelectric structures are piezoelectric fibers or particles and are oriented and poled in substantially the same direction as the stacked configuration. Piezoelectric particles could also be oriented such that they are not in substantially the same direction as the stacked configuration, but are poled in the direction of the stacked configuration. In further embodiments, the piezoelectric fibers or particles are present at about 10% to about 50% volume fraction of the piezoelectric composite. In still further embodiments, an encapsulation coating can surround an exterior of the composite.

Suitably, the tissue-stimulating piezoelectric composite comprises at least two layers.

In further embodiments, a tissue-stimulating implant comprising the tissue-stimulating piezoelectric composites described herein is provided, suitably wherein the composite is embedded in or attached to the implant.

Also provided are methods of making a piezoelectric composite, the methods comprising preparing a polymerizable matrix, dispersing a plurality of piezoelectric structures in the polymerizable matrix to generate a dispersion, shaping the dispersion, curing the dispersion, cutting the cured dispersion into two or more layers, and stacking the layers substantially adjacent to each other to generate the piezoelectric composite. Exemplary polymers and piezoelectric structures are described herein.

In embodiments of the methods, the shaping comprises injection molding, extrusion, compression molding, blow molding or thermoforming. Suitably, the cutting comprises sawing. The methods can also further comprise encapsulating the piezoelectric composite with an electrically insulating encapsulation coating.

Also provided are tissue-stimulating implants (e.g., spinal implants) comprising a piezoelectric composite, the piezoelectric composite comprising two or more layers, each layer comprising a polymer matrix, and a plurality of piezoelectric structures within the polymer matrix, wherein the layers are substantially adjacent to each other in a stacked configuration. The tissue-stimulating implants further comprise an electrical connection connecting at least two of the layers of the piezoelectric composite, an electrically insulating encapsulation coating surrounding an exterior of the piezoelectric composite, and a power converter electrically connected to the piezoelectric composite.

In suitable embodiments of the tissue-stimulating implants, the piezoelectric structures are piezoelectric fibers or piezoelectric particles, examples of which are disclosed herein. Examples of suitable polymers are also described throughout.

Suitably, the power converter provides an output voltage, suitably having an average voltage of about 0.1 V to about 100 V, with the voltage pulsed as dictated by the available power from the piezoelectric composite. In further embodiments, the power converter provides a direct current of about 1 µAmp to about 250 µAmp with current pulsed as dictated by the available power from the piezoelectric composite.

In embodiments of the tissue-stimulating implants disclosed herein, the piezoelectric composite comprises at least 2 layers, and suitably the layers are connected mechanically in series and electrically in parallel.

Suitably, the piezoelectric fibers or piezoelectric particles are present at about 10% to about 50% volume fraction of the piezoelectric composite.

In embodiments, the tissue-stimulating implants further comprise a first electrode on an exterior of the electrically insulating encapsulation coating and a second electrode that is attached to an area of tissue at least 1 cm away from the first electrode. The power converter is connected to the encapsulated piezoelectric composite and can be contained within the encapsulation or in a separate encapsulation. The power converter has a positive and negative output that connects separately to the two electrodes. The connection between the two electrodes is made through body tissues. In embodiments, the first and second electrodes, when implanted in a tissue of a patient, are positioned so as to provide direct current to the first electrode.

Further embodiments, features, and advantages of the embodiments, as well as the structure and operation of the various embodiments, are described in detail below with reference to accompanying drawings.

DETAILED DESCRIPTION OF PREFERRED EMBODIMENTS

It should be appreciated that the particular implementations shown and described herein are examples and are not intended to otherwise limit the scope of the application in any way.

The published patents, patent applications, websites, company names, and scientific literature referred to herein are hereby incorporated by reference in their entireties to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Technical and scientific terms used herein have the meaning commonly understood by one of skill in the art to which the present application pertains, unless otherwise defined. Reference is made herein to various methodologies and materials known to those of ordinary skill in the art.

Figure 1B:
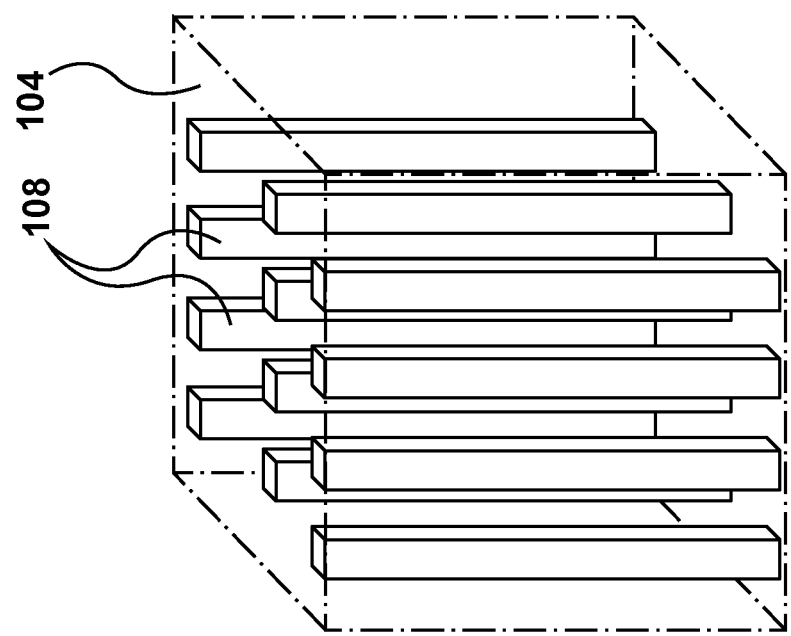
FIGS. 1A and 1B show representations of 0-3 and 1-3 structured composites, respectively.
Figure 1A:
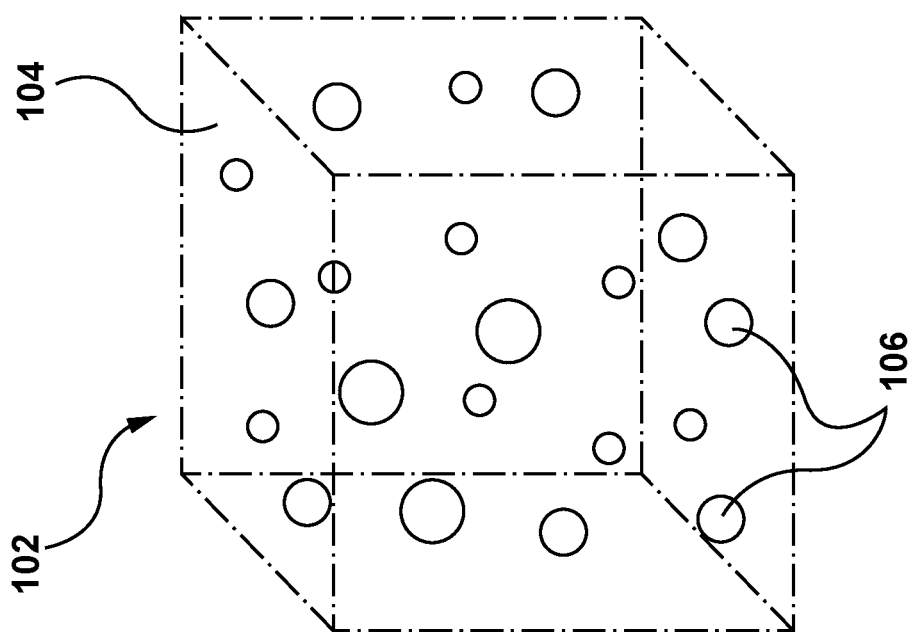

Composite matrices with 0-3 connectivity 102 are typically comprised of particles 106 randomly dispersed within a matrix 104 (FIG. 1A). The matrix 104 is connected to itself in all three spatial directions, while the particles 106 lack contact. As such, effective medium (EM) theory portrays the bulk, or apparent properties of these composites as isotropic. Manufacturing a 0-3 composite is a straightforward process that entails mixing small particle inclusions into a matrix until evenly dispersed. These composites are simple to manufacture in large quantities, typically at low cost. However, when a sufficient number of particles are mixed together in a 0-3 composite, there can be limited 0-3 connectivity.

Orthotropic or transversely isotropic behavior can be induced in a material by inducing structural organization, such as 1-3 connectivity (FIG. 1B). There are several methods of creating 1-3 composites, one example includes wafering a solid material into rod-like 108 structures, and backfilling the voids with the intended material. Others entail weaving fibers 108 through a semi-porous matrix or manually aligning long fibers 108 and then filling the surrounding area with the composite matrix 104. These techniques result in the structures 108 forming continuous columns that span the thickness of the composite.

As described in U.S. Published Patent Application No. 2015/0134061 (the disclosure of which is incorporated herein in its entirety for all purposes), methods utilizing the piezoelectric nature of particles can generate composites with 1-3 connectivity. This is suitably carried out by utilizing piezoelectrophoresis (PEP) or dielectrophoresis (DEP). The PEP force is analogous to the dielectrophoretic force, however, utilization of PEP is accompanied by the added benefit of obviating the need to pole the specimens prior to use. By eliminating the need to apply a large electric field to the sample to induce net piezoelectricity, this technique allows the creation of large scale piezoelectric materials. Furthermore, it allows the use of new matrix materials, previously infeasible due to low dielectric strengths.

Figure 2:
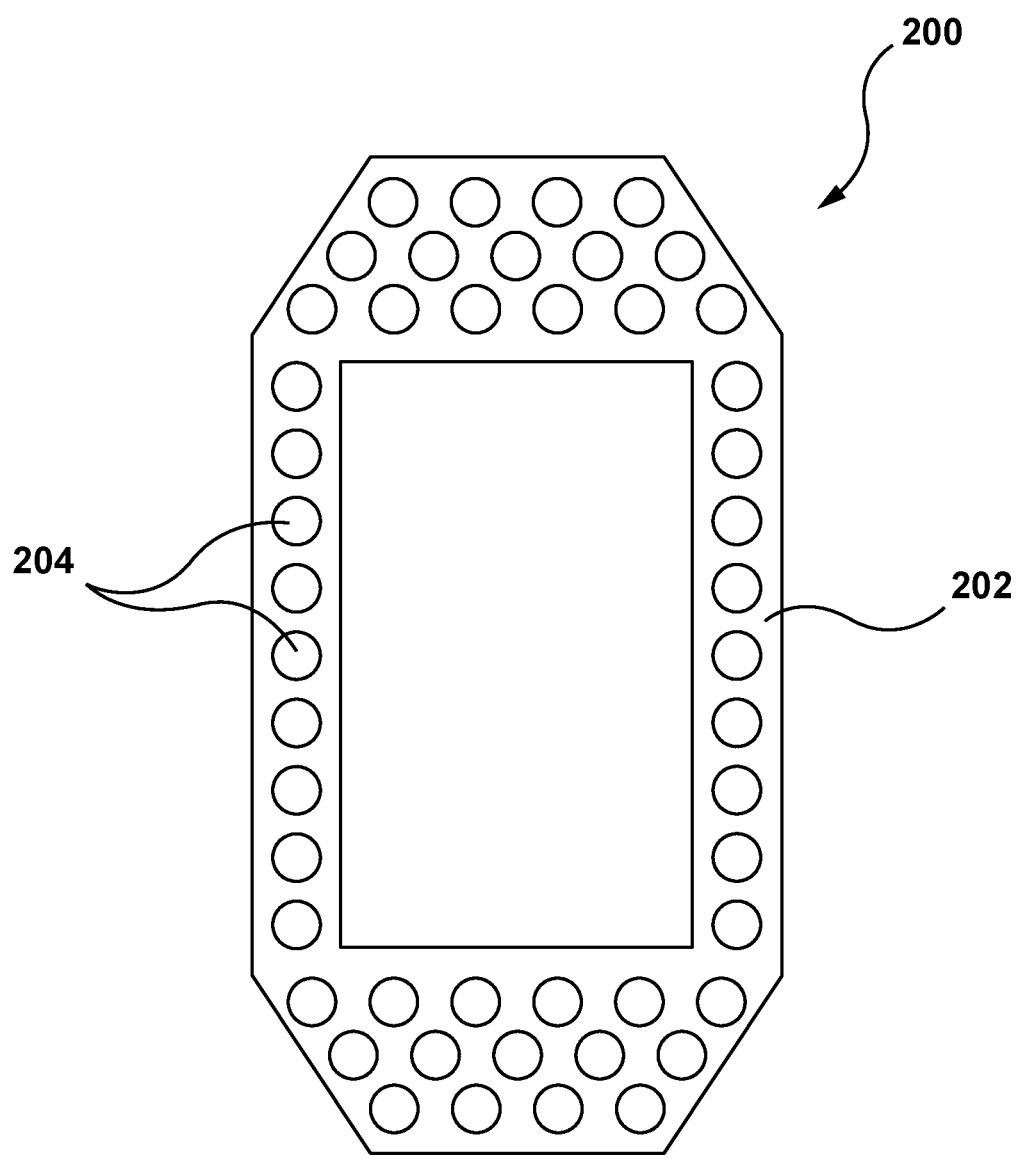
FIG. 2 shows a cross-section of a piezoelectric composite of an embodiment described herein.

In embodiments, piezoelectric composites are provided herein, as shown in FIG. 2 for example. Suitably, the piezoelectric composites comprise two or more layers 200, each layer comprising a polymer matrix 202 and a plurality of piezoelectric structures 204 within the polymer matrix.

As used herein, a "composite" means a material comprising two or more components mixed or dispersed together. As used herein, a "piezoelectric" is a material that is capable of generating a voltage when a mechanical force is applied to the material. As used herein, a "piezoelectric structure" refers to a formed material (i.e. material having a particular shape and dimensions) that is capable of generating a voltage when a mechanical force is applied to the material.

As used herein, "a polymerizable matrix" or "polymer matrix" means a composition comprising monomers, polymers (two or more repeating structural units) or mixtures of monomers and polymers, or copolymers that can form a homogeneous or heterogeneous bulk composition when polymerized.

In suitable embodiments, as shown in FIG. 3, the piezoelectric composites comprise layers 200 which are substantially adjacent to each other in a stacked configuration 300.

Figure 3A:
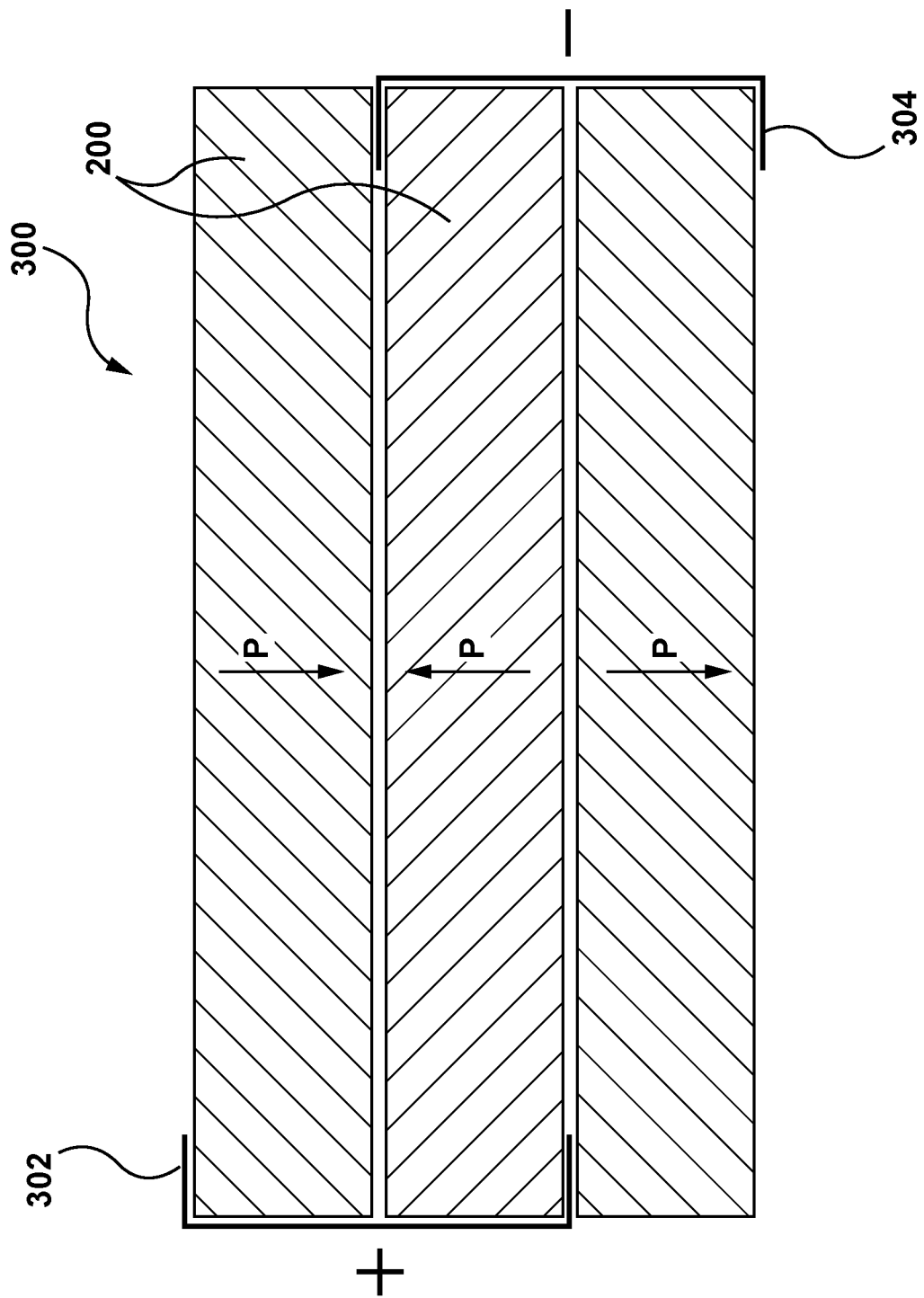
FIGS. 3A and 3B show side views of a stacked piezoelectric composite of an embodiment described herein.

As shown in FIG. 3A, in embodiments, layers 200 comprise individual, separate piezoelectric composite elements, comprising a polymer matrix 202 and a plurality of piezoelectric structures 204 within the polymer matrix. In other embodiments, layers 200 can be a single (or multiple) piezoelectric composite that is folded upon itself (see FIG. 3D) so as to result in a layered structure, in which one portion of the piezoelectric composite is substantially adjacent to another portion of the same piezoelectric composite in a layered fashion (the result is also a stacked configuration). In exemplary embodiments, a mechanical connection is formed between piezoelectric structures 204 and layers 200, in the form of the composite (i.e., a mechanical and structural bond or association is formed between the piezoelectric structure and the polymerizable matrix). The composites described herein are distinct from situations in which the piezoelectric structures are simply inserted into holes of a pre-formed structure for holding the piezoelectric structures.

As shown in FIG. 3A, stacked configuration 300 is suitably formed by placing two or more layers 200 adjacent one another. In embodiments, stacked configuration 300 can be a spiral, helical or corkscrew-type arrangement (see FIG. 3C, with the important structural feature being that layers 200 are configured adjacent to each other. Suitably layers 200 are adjacent to each other, with no intervening material. However, in other embodiments, a spacer element can be placed between layers 200, such as for example, an additional polymeric material or coating, or in suitable embodiments, an adhesive (e.g., an epoxy) can be used to bond the adjacent layers to each other. In such embodiments where a spacer element is used, the layers are also substantially adjacent to one another. In further embodiments, a layer of conductive material (e.g., a 100 nm thick sputter coated layer of gold, gold foil, or other suitable metal) is suitably added to both the top and bottom of layers 200 to ensure electrical connectivity between all piezoelectric structures in each layer.

As used herein, "plurality" refers to 2 or more, suitably 5 or more, 10 or more, 50 or more, 100 or more, 500 or more, 1000 or more, etc., of an item, for example piezoelectric structures. The piezoelectric structures are dispersed in the matrixes via any suitable method, including mixing, stirring, folding or otherwise integrating the piezoelectric structures in the matrix so as to generate a fairly uniform mixture of the structures, mechanically and structurally associated with the matrix.

In exemplary embodiments, the monomers and/or polymers or copolymers of the polymerizable matrix (polymer matrix 202) comprise a thermoset polymer, copolymer and/or monomer, a thermoplastic polymer, copolymer and/or monomer; or a thermoset/thermoplastic polymer or copolymer blend. Exemplary thermoset and thermoplastic polymers, copolymers and monomers are well known in the art, and include for example, polymers, copolymers and monomers of poly(vinylidene difluoride) (PVDF), poly(urethane), various epoxies (epoxy) (e.g., EPO-TEK® 302-3M; EPOXY TECHNOLOGY, INC, Billerica, Mass.), poly(ethylene), poly(styrene), poly(methyl methacrylate) (PMMA), poly(ether ether ketone) (PEEK), poly(aryletherketone) (PAEK), etc.

In embodiments, piezoelectric structures 204 comprise piezoelectric particles. In other embodiments, piezoelectric structures 204 comprise piezoelectric fibers. In further embodiments, the piezoelectric structures can comprise a mixture of fibers and particles.

As used herein, a "piezoelectric particle" refers to a separate, individual structure of a piezoelectric material. As used herein "particle" includes any shape or configuration of material, including spheres, angular shapes, pieces or fragments of materials, flakes, shavings, chips, etc. Exemplary methods of preparing piezoelectric particles include, for example, the specific methods disclosed in U.S. Published Patent Application No. 2015/0134061, which is incorporated by reference herein in its entirety.

As used herein, a "piezoelectric fiber" refers to an elongated structure (i.e., having a length dimension longer than both the width and depth dimensions) of a piezoelectric material. Piezoelectric fibers suitably comprise a circular diameter, though the piezoelectric fibers can have cross-sections having other shapes, including square, rectangular, triangular, oval, or other abstract shapes.

Suitably, piezoelectric structures for use in the composites described herein exhibit a Perovskite crystalline structure, i.e., the same type of crystal structure as calcium titanium oxide ($CaTiO_3$). In embodiments, suitable piezoelectric structures include but are not limited to, structures of barium titanate, structures of hydroxyapatite, structures of apatite, structures of lithium sulfate monohydrate, structures of sodium potassium niobate, structures of quartz, structures of lead zirconium titanate (PZT), structures of tartaric acid and polyvinylidene difluoride structures. Other piezoelectric structures known in the art can also be used in the composites described herein. Suitably, a single type of piezoelectric structure is used in the composites and methods of making the composites, though in other embodiments, mixtures of different types or classes of piezoelectric structures can also be used.

In embodiments, the piezoelectric structures, as piezoelectric particles, are on the order of less than about 500 µm in size, suitably less than about 100 µm in size, less than about 10 µm, less than about 1 µm, less than about 500 nm, or less than about 100 nm in size. In further embodiments, the piezoelectric structures, as piezoelectric fibers, have a diameter (or cross-sectional measurement) on the order of about 100 µm to about 10 mm, more suitably about 200 µm to about 1 mm, about 400 µm to about 1 mm, about 500 µm to about 900 µm, or about 500 µm, about 600 µm, about 700 µm, about 800 µm, about 900 µm. Suitably, the piezoelectric fibers have a length on the order of about 50 mm to about 500 mm, more suitably about 50 mm to about 400 mm, about 50 mm to about 200 mm, about 100 mm to about 200 mm, or about 100 mm, about 110 mm, about 120 mm, about 130 mm, about 140 mm, about 150 mm, about 160 mm, about 170 mm, about 180 mm, about 190 mm, or about 200 mm.

FIG. 2 shows an exemplary cross-section of a layer 200 of piezoelectric composite as described herein. In embodiments, the cross section shows the orientation of piezoelectric structures 204 (either fibers or particles) oriented in polymer matrix 202. The orientation of piezoelectric structures is suitably random in the polymer matrix, but can also be carefully controlled and structured if desired. Exemplary dimensions are shown in FIG. 2 are for illustrative purposes only. The center portion of layer 200 is open, though in other embodiments, this can be filled with polymer matrix 202 or other material, suitably polymeric.

Figure 4B:
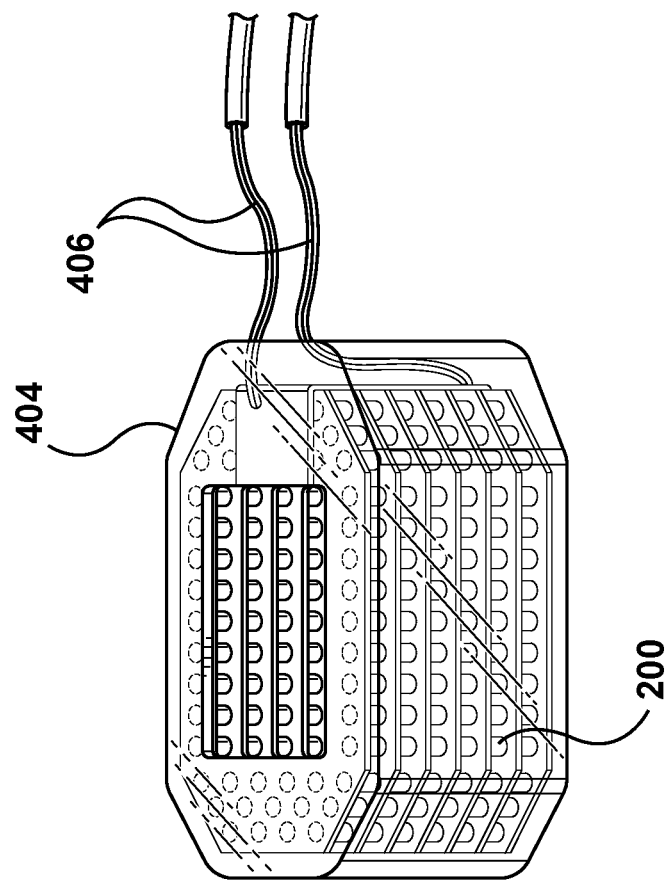
FIGS. 4A and 4B show a stacked piezoelectric composite, and an encapsulated stacked piezoelectric composite, of an embodiment described herein.
Figure 4A:
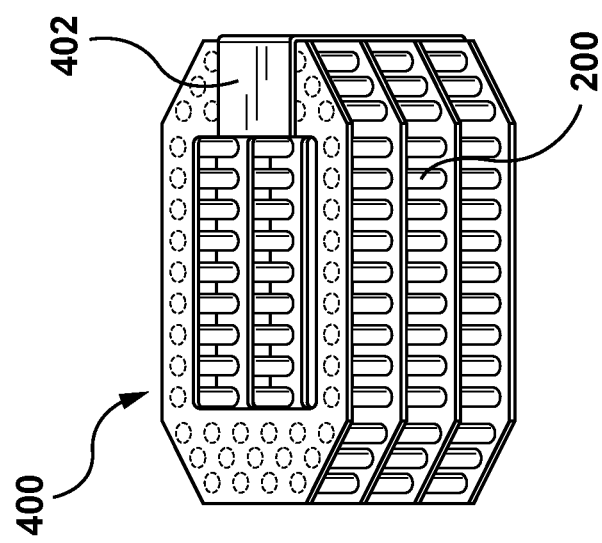
Figure 4C:
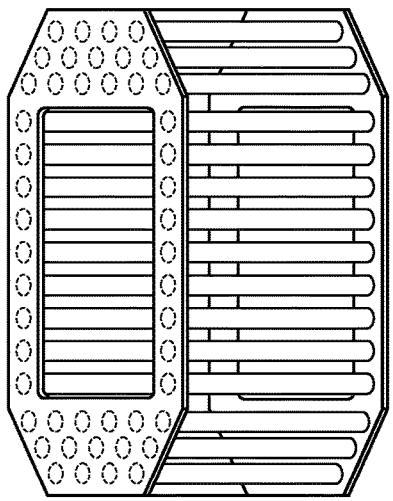
FIGS. 4C-4F show stacked piezoelectric composites having 1, 3, 6 or 9 layers, of an embodiment described herein.
Figure 4D:
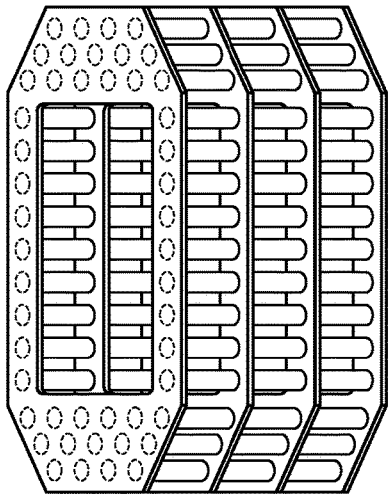
Figure 4E:
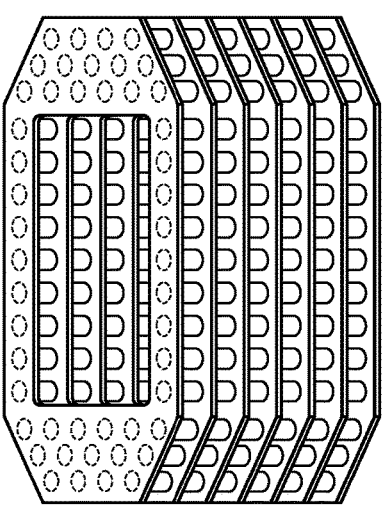
Figure 4F:
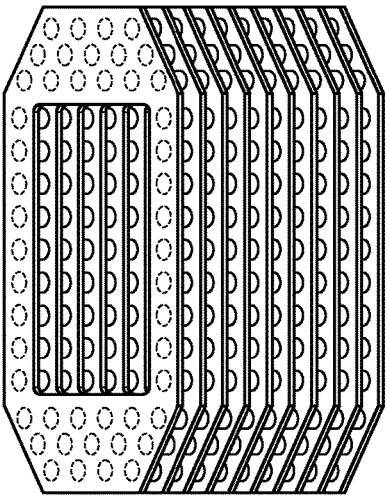

As shown in FIG. 4A, in embodiments, piezoelectric composite 400 (also called composite throughout) suitably comprises layers 200 in a stacked configuration. In FIG. 4A, piezoelectric composite 400 comprises layers 200 comprising piezoelectric fibers in a polymeric matrix. Layers 200 can be attached or adhered to one another simply via polymerizing the layers to form the stacked configuration, or an adhesive or suitable bonding agent can be used. Exemplary adhesives are known in the art, and include for example, various epoxides. Also shown in FIG. 4A is electrical connection 402 that allows for wire(s) 406 to be attached, as in FIG. 4B.

FIG. 4B demonstrates an additional embodiment of the invention, in which an electrically insulating encapsulation coating 404 surrounds an exterior of piezoelectric composite 400.

As used herein "encapsulation coating" includes a thin layer or application surrounding the composite, as well as thicker layers that can provide structural integrity to the composite. The thickness of the encapsulation coating can be on the order of microns or millimeters, up to centimeters, and even 10's to 100's of centimeters. As described herein, suitably the encapsulating coating is electrically insulating, such that the composite is electrically isolated (without the use of a wire or other connection) from the surroundings.

Figure 3B:
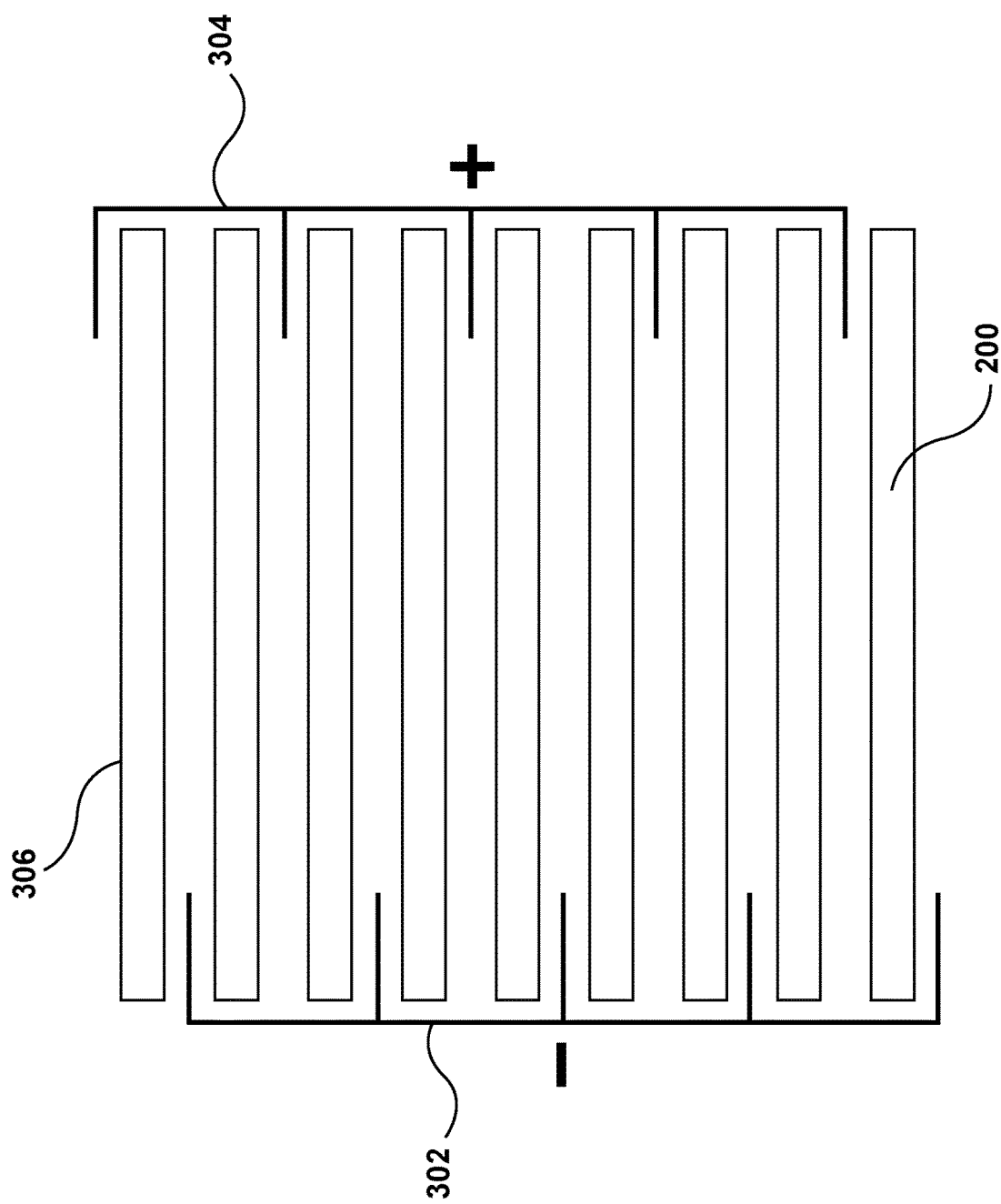
Figure 3C:
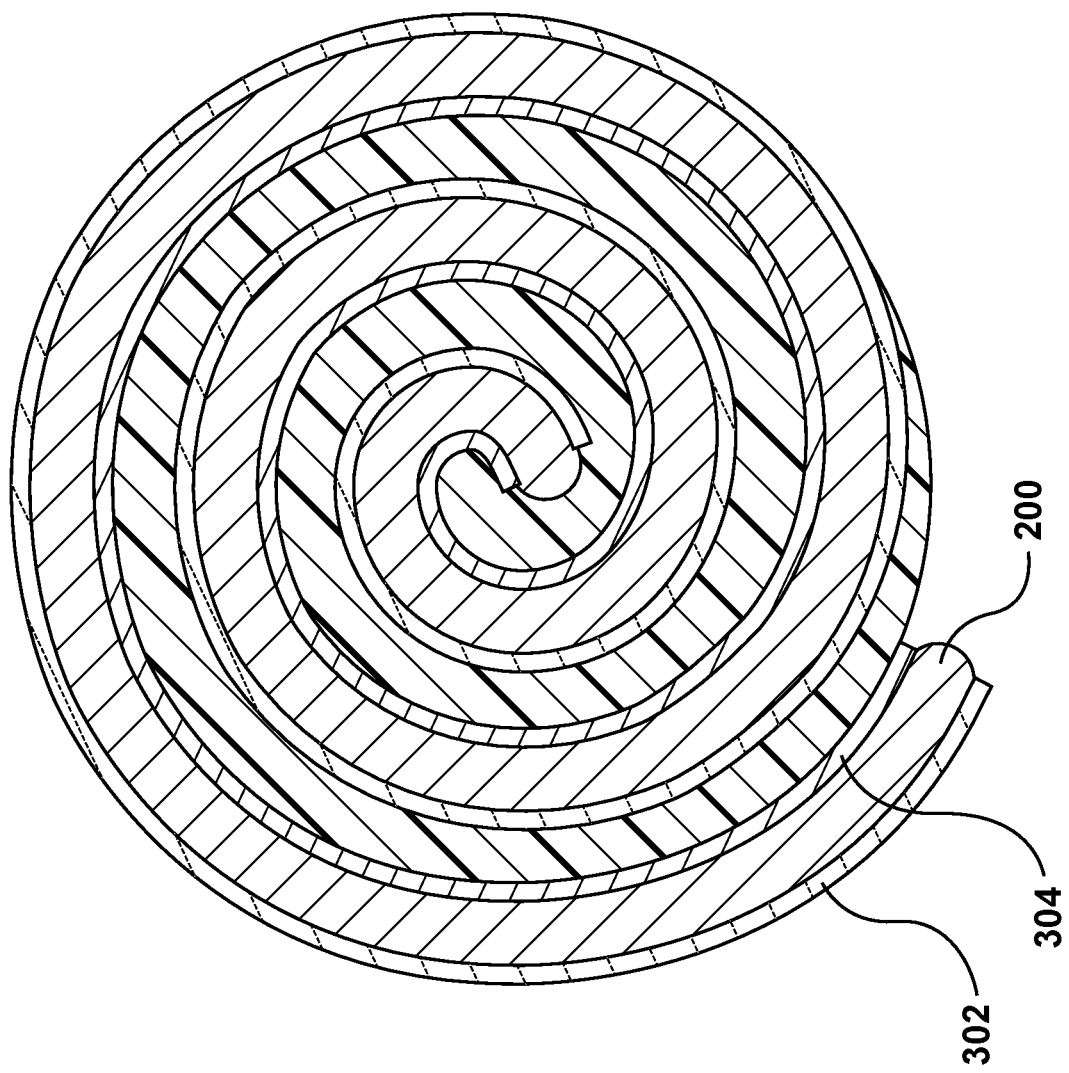
FIG. 3C shows a spiral stacked piezoelectric composite of an embodiment described herein.
Figure 3D:
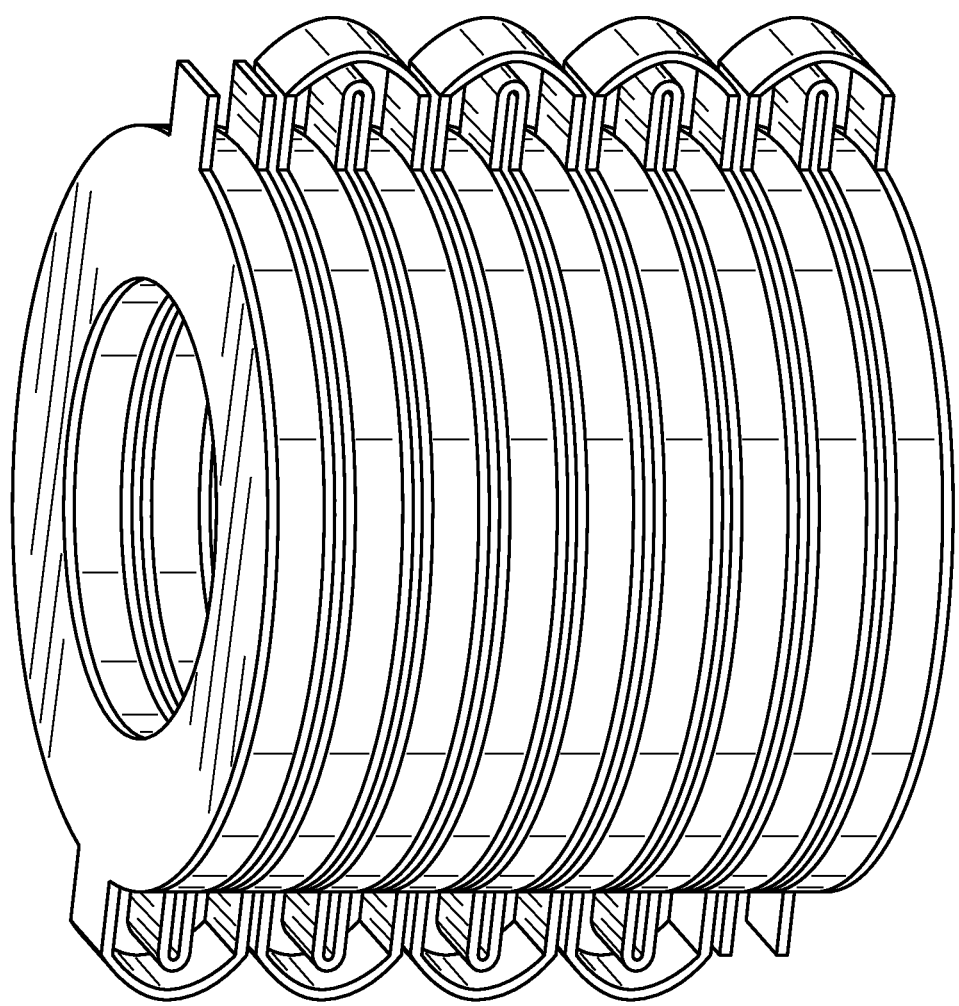
FIG. 3D shows a folded, stacked piezoelectric composite of an embodiment described herein.

In embodiments, as shown in FIG. 3A, suitably layers 200 in a composite 400 are in a stacked configuration 300, and in such a way that the poling of each of the layers is oriented as shown. FIG. 3A also shows an exemplary method for electrically connecting layers 200, suitably by connecting a first two layers with a positive electrical connection 302, and the second and third layers with a negative electrical connection 304. Thus, the layers are suitably connected electrically in parallel and mechanically in series. This orientation can be repeated as needed for additional layers. Electrical connections can be made with various methods know in the art, including for example, the use of conductive wires or tapes (e.g., copper tape) and conductive adhesives. FIG. 3B shows a composite comprising multiple layers 200, each electrically connected in series (electrical connections 302 and 304). Also shown in FIG. 3B is a sputter layer 306 which can be added to each of layers 200 to facilitate attachment of electrical connections 302/304.

In further embodiments, provided herein is a tissue-stimulating piezoelectric composite. As described herein, suitably the tissue-stimulating piezoelectric composite comprises two or more layers, each layer comprising a polymer matrix and a plurality of piezoelectric structures within the polymer matrix. Suitably, the layers are substantially adjacent to each other in a stacked configuration. In embodiments, as described herein, the piezoelectric structures and the polymer matrix are mechanically and structurally connected (i.e. a mechanical and structural bond or association) to form the tissue-stimulating piezoelectric composite.

As used herein, a "tissue-stimulating" composite as described throughout is suitably implanted or otherwise introduced into a patient (including animals or humans) so as to provide electric stimulation to a tissue of a patient when the composite is placed under mechanical loads. Exemplary tissues include, but are not limited to, bone, muscle, cartilage, tendons and organs (e.g., brain, heart, lungs). Electric stimulation may also be provided to cells within the body. Suitably, the patients are mammals, including humans, dogs, cats, mice, rats, monkeys, etc.

In embodiments, the tissue-stimulating piezoelectric composites are bone-stimulating composites, and in exemplary embodiments are spinal implants for spinal fusion. The electric stimulation produced by the composites aids in stimulation of bone growth and osseointegration of the encapsulated composite. Other bone-stimulating implants can also be prepared using dimensions and orientations know in the art as necessitated by the positioning in the body.

As described throughout, suitably the piezoelectric structures in the tissue-stimulating piezoelectric composites are piezoelectric fibers or piezoelectric particles. Exemplary materials for use in the piezoelectric fibers or piezoelectric particles are described herein.

In embodiments, the polymer matrix comprises a thermoset polymer, copolymer and/or monomer, a thermoplastic polymer, copolymer and/or monomer or a thermoset/thermoplastic polymer or copolymer blend. Examples of such materials are described throughout.

In embodiments described herein when piezoelectric fibers are utilized in the composites, suitably the fibers are oriented in substantially the same direction as the stacked configuration, for example as shown in FIGS. 4A-4B. In further embodiments, the particles could be randomly oriented, but have sufficient electrical connectivity and poling so as to act like as though they are oriented in the same direction as the stacked configuration.

As used herein, "oriented in substantially the same direction as the stacked configuration" is used to indicate that the fibers run within the layers in approximately the same direction as layers are stacked. In exemplary embodiments, the fibers are aligned perpendicularly, that is suitably within approximately 0-20° of perpendicular (i.e., 90°) relative to the planes of the upper and lower surfaces of the layers. For example, as shown in FIGS. 4A-4F, fibers are shown oriented in substantially the same direction as the stacked configuration.

In embodiments of the tissue-stimulating piezoelectric composites disclosed herein, the piezoelectric fibers are present at about 1% to about 80% volume fraction of the piezoelectric composite. That is, about 1% to about 80% of the entire volume of the piezoelectric composite (comprising piezoelectric fibers and polymer) is made of piezoelectric fibers. In further embodiments, about 1% to about 70%, about 5% to about 70%, about 5% to about 60%, or about 10% to about 50%, or about 20% to about 40%, or about 10%, about 20%, about 30%, about 40% or about 50% volume fraction of the piezoelectric composite is piezoelectric fibers. Similar volume fractions can also be used with piezoelectric particles.

In embodiments, the tissue-stimulating piezoelectric composite can further comprise an encapsulation coating, surrounding an exterior of the composite. As described herein, this encapsulating coating includes a thin layer or application surrounding the composite, as well as thicker layers that can provide structural integrity to the composite. The thickness of the encapsulation coating can be on the order of microns or millimeters, up to centimeters, and even 10's to 100's of centimeters. As described herein, suitably the encapsulating coating is electrically insulating, such that the composite is electrically isolated (without the use of a wire or other connection) from the surroundings.

Suitably, the tissue-stimulating piezoelectric composites described herein comprise at least 2 layers. In embodiments, the tissue-stimulating piezoelectric composites can comprise at least 3 layers, at least 4 layers, at least 5 layers, at least 6 layers, at least 7 layers, at least 8 layers, at least 9 layers, at least 10 layers, at least 15 layers, at least 20 layers, at least 30 layers at least 40 layers, at least 50 layers, etc. In FIGS. 4C-4F, tissue-stimulating piezoelectric composites comprising 1, 3, 6 and 9 layers are shown as exemplary embodiments. A person of ordinary skill in the art will readily understand that the number of layers can be increased or reduced, simply by preparing thicker or thinner layers within the overall desired dimensions of a piezoelectric composite.

Suitably the thickness of layers 200 of a piezoelectric composite is on the order of millimeters, or in other embodiments, microns. In general, it is desirable to reduce the thickness of layers 200 as much as possible, and increase the total number of layers as much as possible, so as to have the overall impedance of the tissue-stimulating piezoelectric composite match as closely as possible the impedance of the position within the body where it is being inserted. Suitably, this is in the range of about 1Ω to about 100 kΩ, or about 1Ω to about 40 kΩ and depends on the area of insertion as well as the amount of tissue present near the implant and that is being stimulated. In embodiments, the overall impedance of the tissue-stimulating piezoelectric composite can be higher than 100 kΩ. In embodiments, the thickness of layers 200 is less than about 1 cm, more suitably less than about 50 mm, less than about 30 mm, less than about 20 mm, less than about 10 mm, less than about 5 mm, less than about 1 mm, less than 50 µm, or about 10 µm to about 5 mm, about 50 m to about 5 mm, or about 50 m to about 1 mm.

In still further embodiments, the tissue-stimulating piezoelectric composites can be embedded or attached to a tissue-stimulating implant. Methods for embedding or attaching a tissue-stimulating piezoelectric composite to a tissue-stimulating implant include polymerization of the implant around the composite, use of adhesive or similar bonding agent, or use of screws or other similar mechanical connection devices.

In further embodiments, provided herein are methods of making a piezoelectric composite. In embodiments, the methods comprise preparing a polymerizable matrix, dispersing a plurality of piezoelectric structures in the polymerizable matrix to generate a dispersion, shaping the dispersion, curing the dispersion to create a mechanical and structural bond or association between the piezoelectric structures and the polymerizable matrix, cutting the cured dispersion into two or more layers and stacking the layers substantially adjacent to each other to generate the piezoelectric composite.

Exemplary polymerizable matrixes are described herein. Dispersion of piezoelectric structures (e.g., fibers or particles as described herein) in the polymerizable matrix suitably comprises addition of such structures, and in the case of fibers, aligning the structures so as to maintain substantially aligned fibers with electrical connectivity. In the case of particles, some mixing in the dispersion may be required to prepare a homogenous dispersion, or largely homogenous dispersion, where the particles are distributed throughout (or throughout a majority of) the polymerizable matrix. In embodiments, both fibers and particles can be added.

As used herein, "shaped" or "shaping" refers to a mechanical or physical process by which a matrix (or dispersion) is changed to a desired form. "Shaping" can also include simply placing a matrix into a desired container or receptacle, thereby providing it with a maintained shape or form. It should be noted that the shaped form is not necessarily the final form, as additional processing (e.g., machining, forming, etc.) can be completed on the final, cured composite. The act of shaping the dispersion for use in the methods described herein is primarily to give some initial structure to the dispersion prior to further processing. A rigid or specific shape is not required.

Exemplary methods of shaping the dispersions comprising the piezoelectric structures and polymerizable matrix include, but are not limited to, injection molding, extrusion, compression molding, blow molding or thermoforming. Other suitable shaping methods can also be used. In other embodiments, the dispersion can simply be placed in a suitable container or other receptacle to hold the dispersion while the various other steps of the methods described herein are carried out.

The dispersion is then cured to create a piezoelectric composite. Exemplary methods of curing the polymerizable matrices so as to form the final composite are known in the art, and include, but are not limited to, cooling, UV curing, heat accelerated curing or compression curing of the dispersion. As described herein, this curing results in a mechanical and structural bond or association between the piezoelectric structures and the polymerizable matrix.

Methods of cutting the cured dispersion in to two or more layers include, for example, use of various cutting knives or saws, including diamond saws, etc. The layers resulting from the cut dispersions are then stacked sufficiently adjacent to each other to generate the piezoelectric composite. Stacking also suitable includes formation of a spiral or similar structure of the piezoelectric composite layers. In embodiments, an adhesive or bonding layer (e.g., a polymer such as an epoxy) is used to bond the layers together. In further embodiments, a layer of a metal (e.g., sputter coated gold or gold foil) is suitably added to the top and/or bottom of the layers prior to the stacking.

In further embodiments, as an alternative to cutting the cured dispersion into separate layers, the dispersion can simply be folded or otherwise formed into a structure that contains layers aligned adjacent to each other in a stacked configuration. As described herein, additional configurations, such as a spiral configuration, can also be utilized.

Exemplary polymerizable matrices for use in the methods are described herein, and include for example, a thermoset polymer, copolymer and/or monomer, a thermoplastic polymer, copolymer and/or monomer, or a thermoset/thermoplastic polymer or copolymer blend.

Suitable materials for use in the piezoelectric structures utilized in the methods are described herein and can comprise lead zirconium titanate or barium titanate or any other piezoelectric materials.

In additional embodiments, the methods further comprise encapsulating the piezoelectric composite with an encapsulation coating. Such methods can suitably include the use of an applicator (e.g., a brush, roller or similar device), or spray to generate an encapsulation coating, or can comprise simply placing the piezoelectric composite into, and withdrawing from or leaving in, a liquid solution (e.g., a polymer, such as epoxy), and then allowing the polymer to cure so as to generate the encapsulation coating. As described herein, an encapsulating coating includes a thin layer or application surrounding the composite, as well as thicker layers that can provide structural integrity to the composite. The thickness of the encapsulation coating can be on the order of microns or millimeters, up to centimeters, and even 10's to 100's of centimeters. As described herein, suitably the encapsulating coating is electrically insulating, such that the composite is electrically isolated (without the use of a wire or other connection) from the surroundings.

Figure 6:
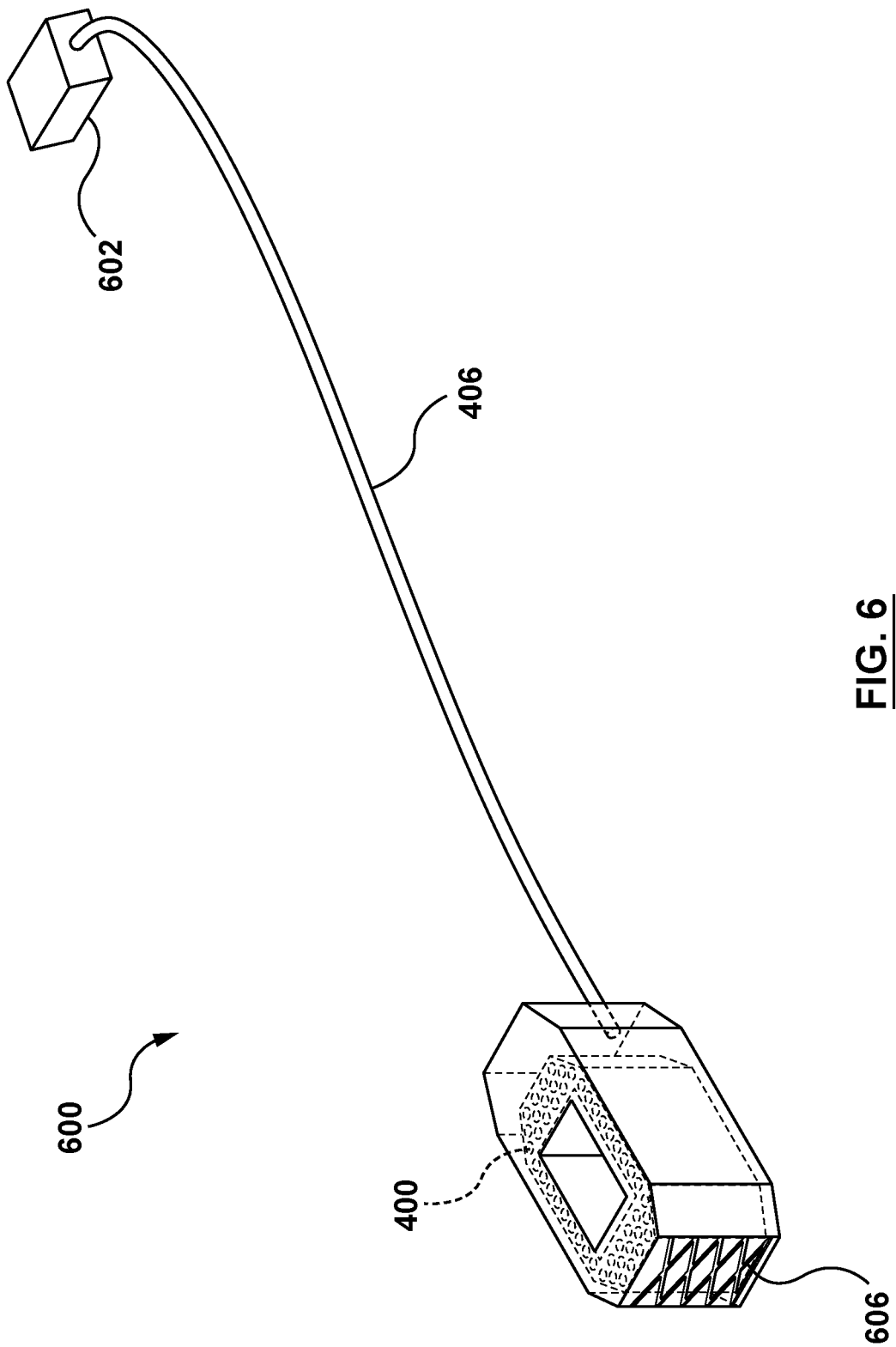
FIG. 6 shows a tissue-stimulating implant of an embodiment described herein.

Also provided herein are tissue-stimulating implants 600, for example as shown in FIG. 6. Suitably, the implants comprise a piezoelectric composite 400. As described herein, suitably the piezoelectric composite comprises two or more layers 200. In embodiments, each layer comprises a polymer matrix and a plurality of piezoelectric structures (e.g., particles, or fibers, or mixtures) within the polymer matrix. Suitably, the layers are substantially adjacent to each other in a stacked configuration.

The tissue-stimulating implants suitably also comprise an electrical connection 402 connecting at least two of the layers of the piezoelectric composite. In embodiments, the implants suitably comprise an encapsulation coating 404 surrounding an exterior of the piezoelectric composite.

As shown in FIG. 6, a power converter 602 is electrically connected (e.g., via wire(s) 406) to the piezoelectric composite and to the electrode 606.

As described throughout, suitably the piezoelectric fibers are oriented in substantially the same direction as the stacked configuration. Exemplary polymers for use in the polymer matrix and encapsulation coating are described herein, as are suitable materials for use as piezoelectric structures (e.g., particles, fibers, or mixtures thereof).

In embodiments, power converter 602 provides a pulsed output voltage with a maximum set voltage. The pulsed output can instead be a constant voltage output depending on the power input from the piezoelectric composite. In suitable embodiments, power converter 602 is a hysteretic power converter, suitably a micropower (µPower) hysteretic power converter (or simply hysteretic converter). Power converter 602 is suitably a switch-mode power supply capable of single digit microwatt power accumulation and pulsed output delivery. Power converter 602 is suitably designed to drive a variable load resistance at a static DC output (pulsed), in the range of 1 µAmp to about 250 µAmp with current pulsed as dictated by the available power from the piezoelectric composite. In embodiments, the DC current is in the range of about 0.1 µAmp to about 500 µAmp, or about 1 µAmp to about 300 µAmp, about 1 µAmp to about 250 µAmp, about 10 µAmp to about 200 µAmp, about 50 µAmp to about 200 µAmp, or about 50 µAmp, about 60 µAmp, about 70 µAmp, about 80 µAmp, about 90 µAmp, about 100 µAmp, about 110 µAmp, about 120 µAmp, about 130 µAmp, about 140 µAmp, about 150 µAmp, about 160 µAmp, about 170 µAmp, about 180 µAmp, about 190 µAmp, about 200 µAmp, about 210 µAmp, about 220 µAmp, about 230 µAmp, about 240 µAmp, or about 250 µAmp. Suitable voltages are about 1 mV to about 50 V, more suitably about 10 mV to about 10 V, about 100 mV to about 10 V, about 500 mV to about 10 V, about 1 V to about 10 V, about 2 V to about 10 V, about 2 V to about 7 V, or about 1 V, about 2V, about 3 V about 4 V, about 5 V, about 6 V, about 7 V, about 8 V, about 9 V or about 10 V.

Power converter 602 suitably accumulates energy on low leakage input storage capacitors until a predetermined voltage threshold is reached (e.g., about 4-5V), causing the storage capacitors to be discharged into the load. Power converter 602 is suitably designed specifically to operate with both resonant and non-resonant piezoelectric generators. Generator input powers ranging from about 1 µW to about 50 mW are suitably compatible with power converter 602.

Figure 5A:
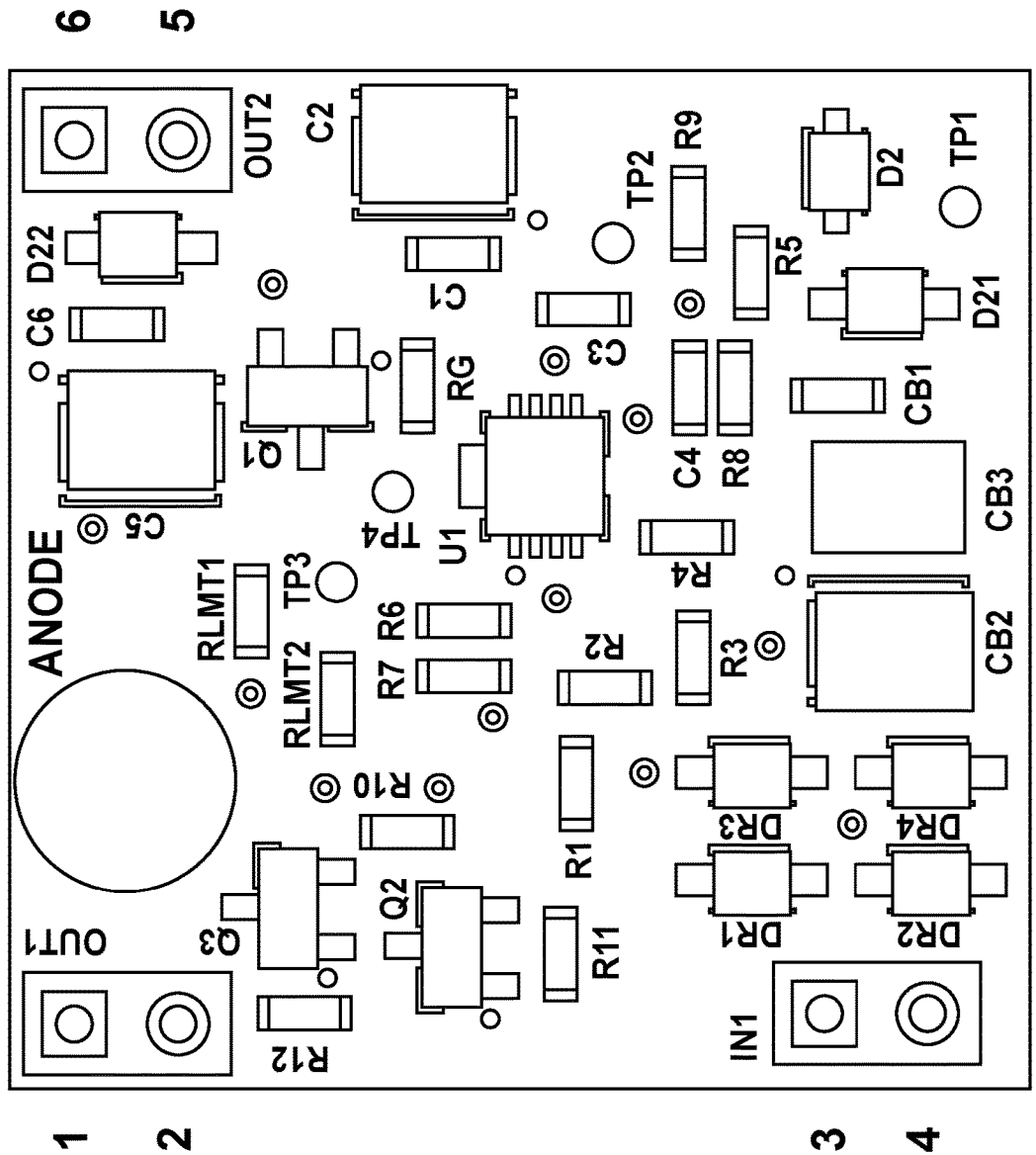
FIG. 5A shows a pin allocation of a power converter of an embodiment described herein.
Figure 5B:
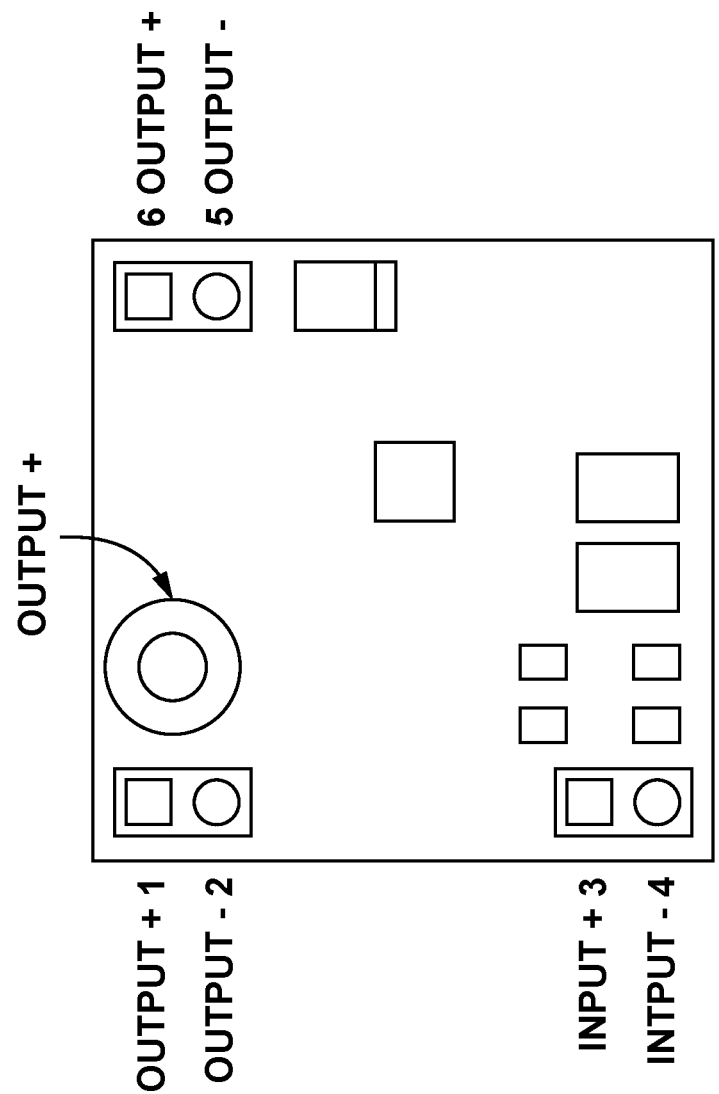
FIG. 5B shows a captive nut diagram of a power converter of an embodiment described herein.
Figure 5C:
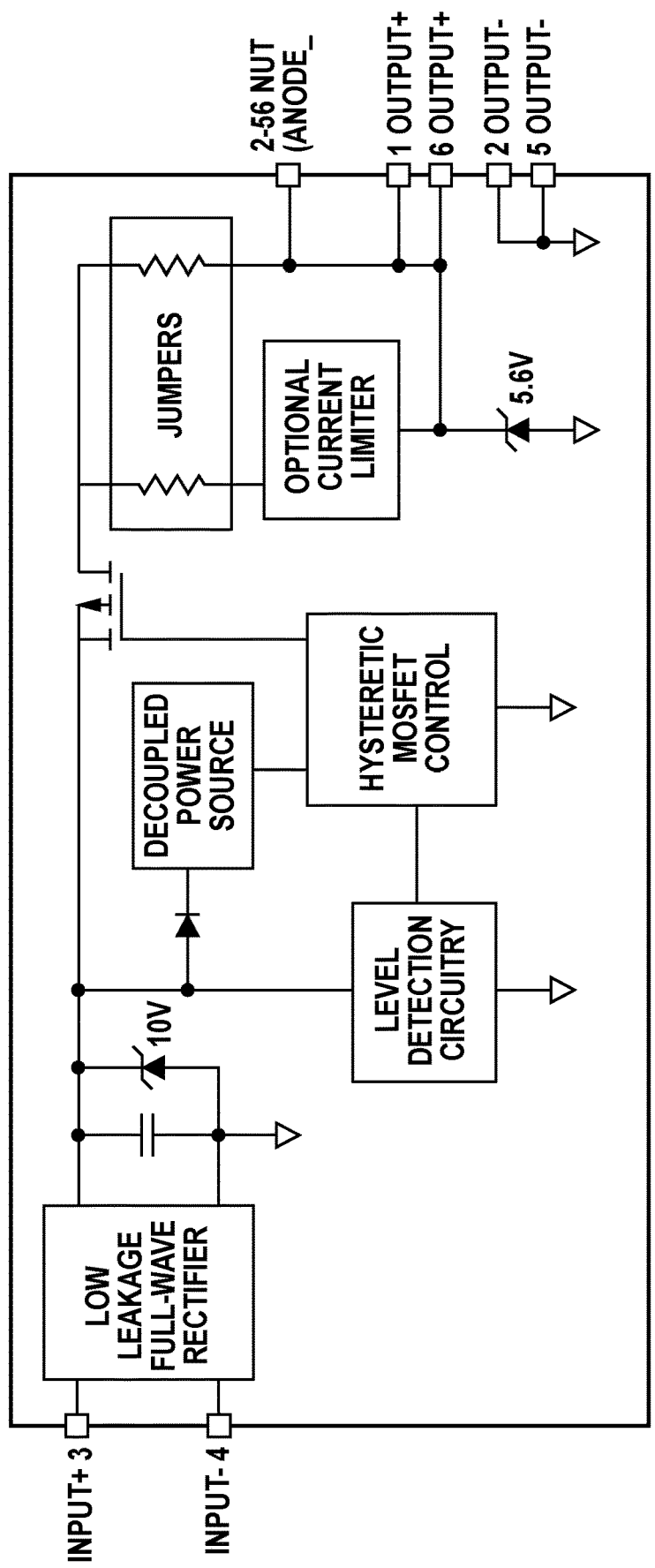
FIG. 5C shows an exemplary block diagram of a power converter of an embodiment described herein.
Figure 5D:
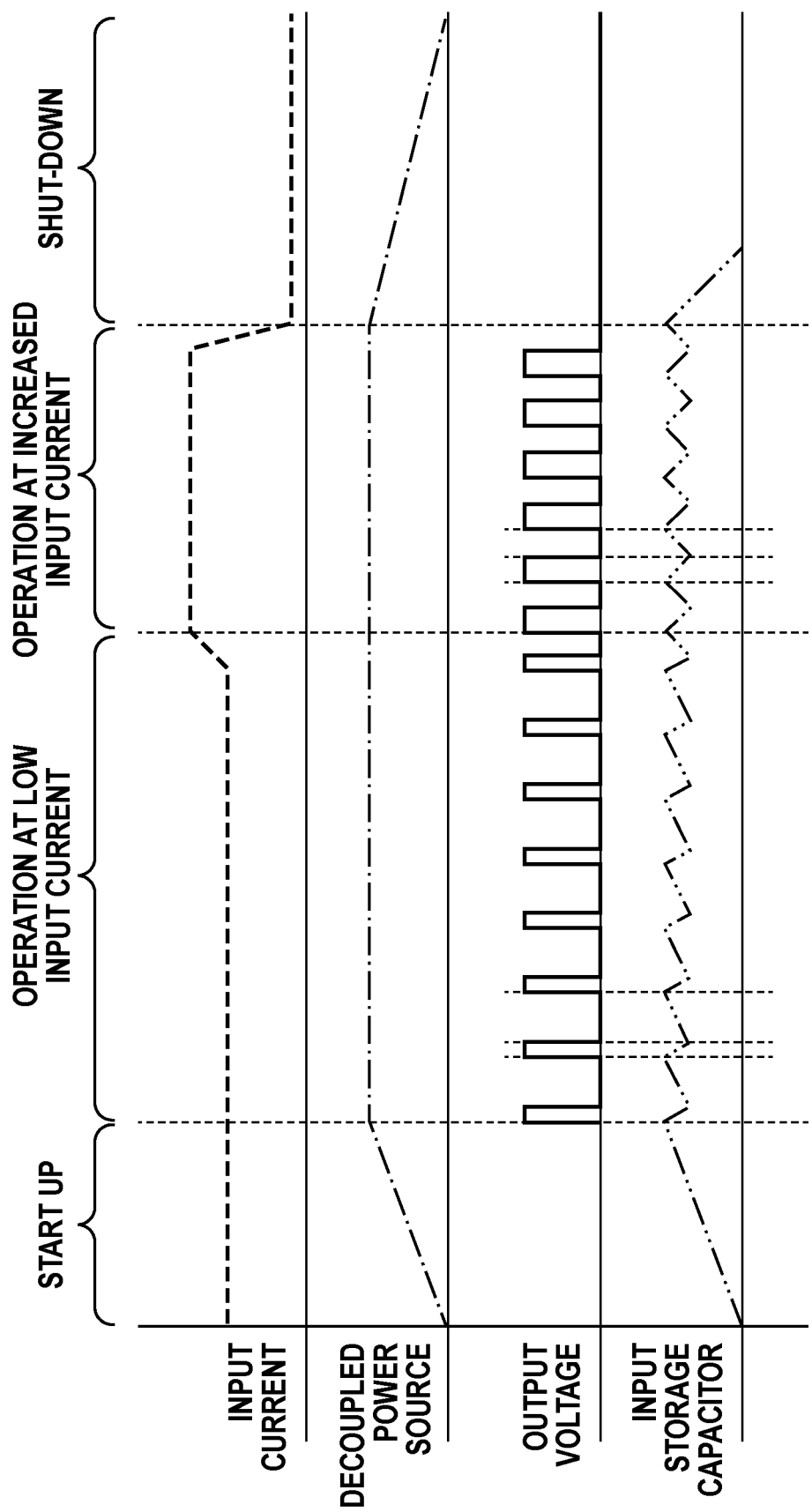
FIG. 5D shows an exemplary timing diagram of a power converter of an embodiment described herein based on theoretical power generated by the piezoelectric composite.

FIG. 5A shows a diagram of a suitable pin allocation for power converter 602. FIG. 5B shows a captive nut diagram of power converter 602. Suitable power converters can be prepared using engineering designs from, for example, Qor-Tex, Williamsport, Pa.

Table 1 provides exemplary ratings for power converter 602.

TABLE 1

| Exemplary Ratings | |
|---|---|
| Characteristic | Value |
| Input+ to Input− | ±50 V DC |
| Input Supply Current | 100 mA (150 mA input peak) |
| Output Current | 100 mA (continuation average); 700 mA Peak |
| Maximum Power Dissipation | 200 mW (input/output Stage Zener at 25° C.); Power MOSFET 350 mW (25° C.); Power MOSFET 185 mW (85° C.) |
| Temperature Range | 0-75° C. (Operation); 0-125° C. (Storage) |

Table 2 shows exemplary electrical characteristics of power converter 602. It should be noted that these characteristics are illustrative and can be modified as desired by a person of ordinary skill in the art.

TABLE 2

| Electrical Characteristics of Power Converter | | | | | |
|---|---|---|---|---|---|
| PARAMETER | TEST CONDITIONS | MIN | TYP | MAX | UNIT |
| $I_{out}$ Output Current | | — | — | 700 | mA |
| $V_{in}$ Input Voltage Range | | 5.6 | | 50 | VDC |
| $V_{out}$ Output Voltage Range | NOTE: Output voltage set by device hysteresis, heavy loads will result in significant output drop, due to minimum pulse width (80 µs). | 2 | 5 | 5.1 | V |

TABLE 2-continued

Electrical Characteristics of Power Converter

| PARAMETER | TEST CONDITIONS | MIN | TYP | MAX | UNIT |
|---|---|---|---|---|---|
| $\eta_s$ Efficiency (System) | 5 µA Input Current | 12 | 22 | 32 | % |
| | 12 µA Input Current | 35 | 40 | 50 | |
| | 25 µA Input Current | 58 | 60 | 62 | |
| | 50 µA Input Current | 71 | 72 | 73 | |
| | 100 µA Input Current | 75 | 76 | 78 | |
| $I_{lim}$ Output Current Limit | NOTE: Current limited by input energy storage and input current maximum rating. | | N/A | | A |
| $I_{ir}$ Inrush Current | Variable | | See $T_{ON}$ | | A |
| $t_{ir}$ Inrush Current Time | Variable | | See $T_{ON}$ | | s |
| $F_s$ Switching Frequency | NOTE: Pulsed output variable switching frequency based on electrical load/input current. Lighter load generally equals faster switching frequency. | 100 | 1k | 5k | Hz |
| $C_{I\,(int)}$ Internal Input Capacitance | | | 0.1 | | µF |
| $T_{ON}$ Start-up Time | 3 µA Input Current | | 10 | | s |
| | 5 µA Input Current | | 4.2 | | s |
| | 10 µA Input Current | | 1.8 | | s |
| | 20 µA Input Current | | 0.872 | | s |
| $T_{OFF}$ Shut-Down Time | 100% Discharge (at open circuit) | | 35 | | s |
| | 50% Discharge (at open circuit) | | 7 s | | s |
| $P_{HI}$ Positive Pulse-Width | | 70 | 80 | 90 | µs |

FIG. 5 C shows an exemplary block diagram of power converter 602.

FIG. 5 D shows an exemplary system timing diagram of power converter 602. As demonstrated in FIG. 5D, the input storage capacitor is charged via piezoelectric composite 400 (see FIG. 6), via connecting wire 604, building up stored power in the capacitor. When the capacitor reaches a desired voltage, a switch is turned on, and the capacitor is discharged in a short pulse (pulse width on the order of 10-100 microseconds, suitably about 50 to 100 microseconds, more suitably about 70-90 microseconds; voltage on the order of about 1-10V DC, suitably about 5V). The switch turns back off, the capacitor recharges, and the cycle is repeated.

In other embodiments, a constant current/voltage can be delivered without a pulse, instead providing a constant output to the power converter and the electrodes as described herein.

As the capacitor is charged (and thus discharges) in response to the power generated by the piezoelectric composite, in embodiments where the composites are implanted in the body of a patient, the more movement (i.e., more walking) that occurs, the more faster the power is generated to the patient in the form of the pulsed discharges. The pulsed nature of the power delivered to the body in which the composite is implanted is believed to improve healing, and may be due to the repetitive nature of the pulse, the pulse length, and/or the timing of the pulses with respect to the movements of the body. That is, it is believed that a pulsed direct current may be more beneficial than a constant direct current for healing of tissue and bone where the implants are positioned.

As described throughout, it is desirable to use the thinnest possible layers, and to increase the number of layers as high as possible, so as to reduce the impedance mismatch between the composite and the tissue in which the piezoelectric composite is implanted. In embodiments, more than 4 layers are utilized, suitably more than 5 layers, more than 10 layers, more than 20 layers, more than 30 layers, etc. are utilized. In embodiments, suitably between 6 and 10 layers are utilized in the piezoelectric composites. As described herein, suitably the layers are connected mechanically in series and electrically in parallel.

In embodiments of the tissue-stimulating implants described herein, the fibers are present at about 1% to about 70% volume fraction of the piezoelectric composite. That is, about 1% to about 70% of the entire volume of the piezoelectric composite (comprising piezoelectric fibers and polymer) is made of piezoelectric fibers. In further embodiments, about 5% to about 60%, or about 10% to about 50%, or about 20% to about 40%, or about 10%, about 20%, about 30%, about 40% or about 50% volume fraction of the piezoelectric composite is piezoelectric fibers. Similar volume fractions can be used with piezoelectric particles.

Suitably, an electrode is connected to on an exterior of the encapsulation coating electrically connected to the power converter 602, suitably via wire 604. As shown in FIG. 6, suitably a negative electrode 606 (electrode proving the stimulation) is positioned on the piezoelectric implant 400 such that it is placed surgically at the anterior aspect of the spinal column, and wire 604 is attached to the posterior of piezoelectric implant 400, which then connects to power converter 602 with the positive terminal that is located away from the implant at the end of the wire 406.

Placement of negative electrode 606 and connection to positive electrode (in 602) are suitably positioned so provide a maximum benefit to the tissue and patient into which the piezoelectric composite is implanted.

Negative and/or positive electrode (606/602) do not have to be placed in physical contact with a bone tissue to provide a desired benefit to the patient. The electrodes can be in close proximity to the bone, as one mechanism of action is to change the pH local to a bone, thus stimulating the bone to produce its BMP. The pulsed mechanism that is in synch with a mechanical loading can also provide negatively charged ions that may act bind up other bone inhibiting molecules (positively charged Sclerostin) that are formed as a result of dynamic mechanical loading (i.e., the "pulsed" connection) that would otherwise inhibit another mechanism of building bone. (See Morse, A., McDonald, M. M., Kelly, N. H., Melville, K. M., Schindeler, A., Kramer, I., Little, D.

G. (2014), "Mechanical Load Increases in Bone Formation via a Sclerostin-Independent Pathway," *Journal of Bone and Mineral Research: The Official Journal of the American Society for Bone and Mineral Research*, 29(11), 2456-2467; and Cejka D, Marculescu R, Kozakowski N, Plischke M, Reiter T, Gessl A, and Haas M. (2014) "Renal Elimination of Sclerostin Increases With Declining Kidney Function," *Clin Endocrinol Metab*, 99(1):248-255.)

In general, the current provided by the tissue-stimulating implants described herein are able to influence a volume approximately equal to a sphere of about 5-8 mm in diameter surrounding the electrode. Thus, it is desirable to locate electrodes carefully, and in very specific locations where stimulation is desired.

Figure 7A:
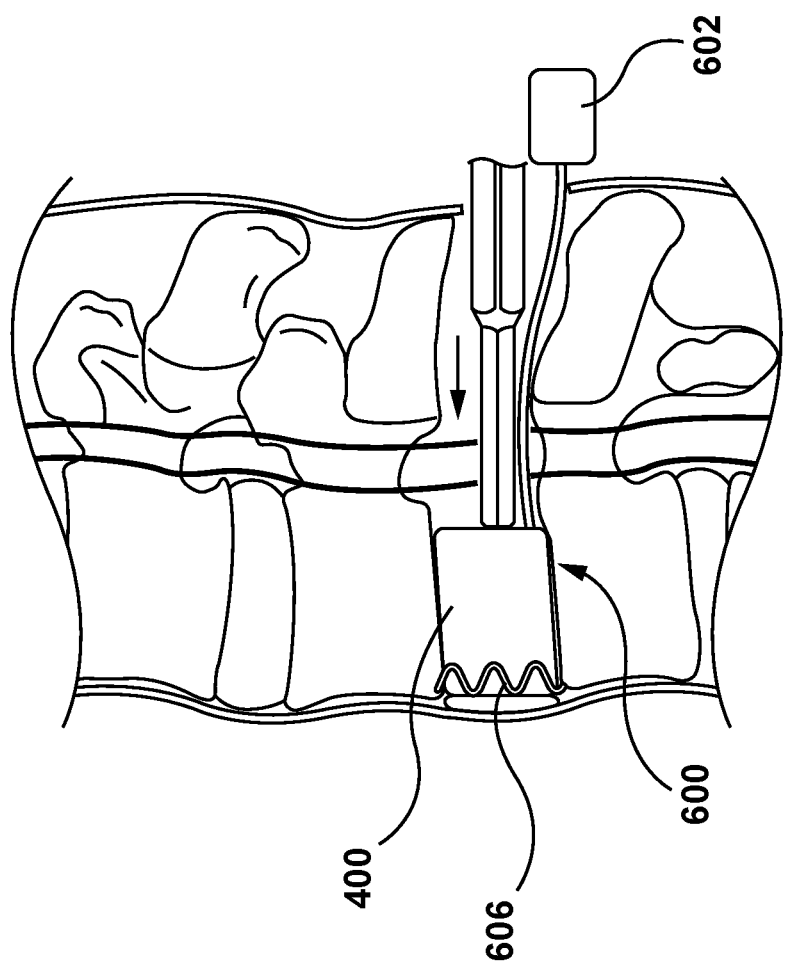
FIG. 7A shows the positioning of a tissue-stimulating implant of an embodiment described herein.
Figure 7B:
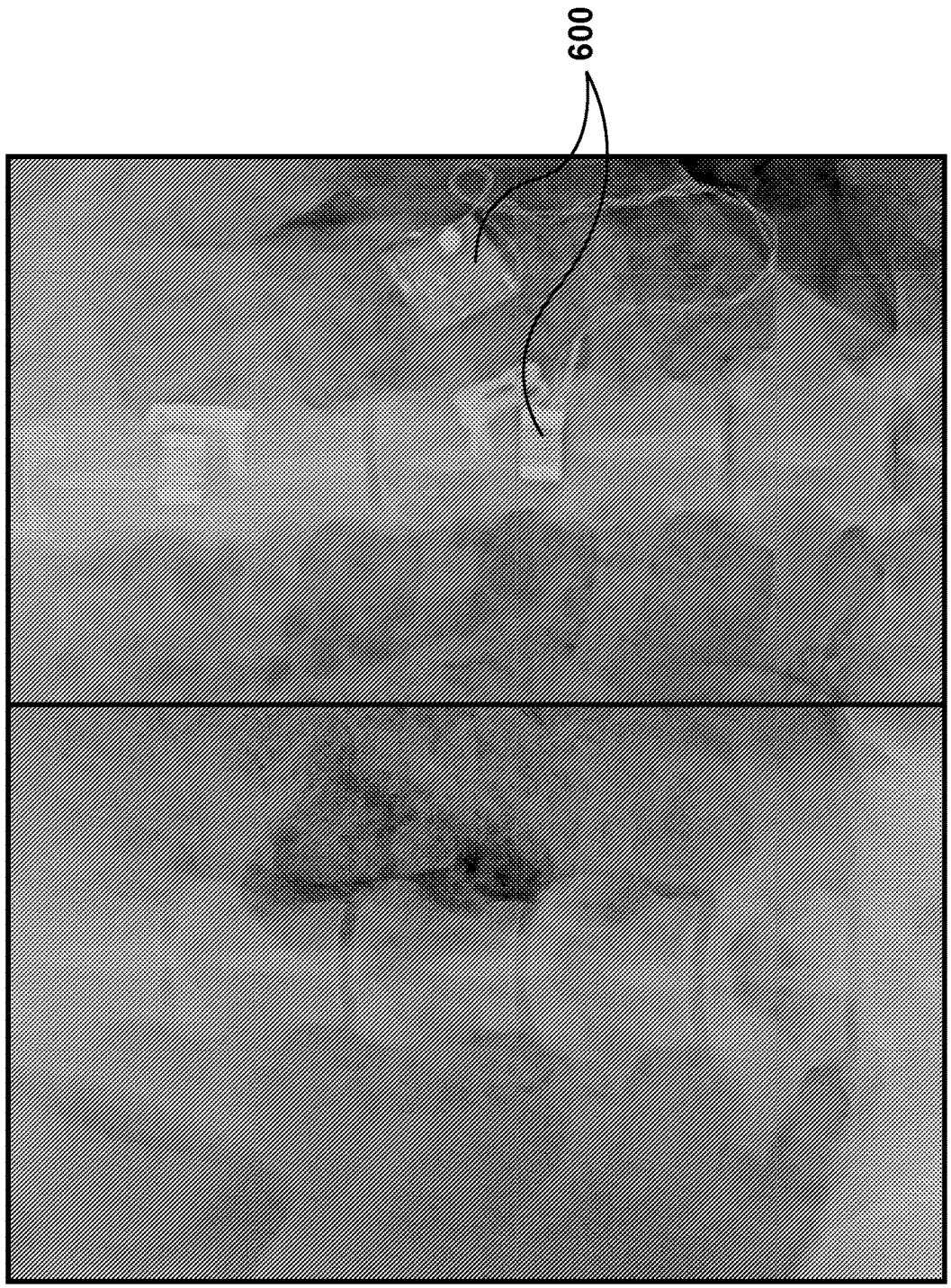
FIG. 7B shows an X-ray of the positioning of a tissue-stimulating implant of an embodiment described herein.

As shown in FIG. 7A, tissue-stimulating implant 600, if utilized as a fusion spinal implant, is suitably positioned so that the bone stimulating (negative) electrode 606 is positioned anterior, i.e., away from the spinal cord, while the positive terminal and power converter 602 is attached in adjacent soft tissue. FIG. 7B shows an X-ray demonstrating the positioning of the tissue-stimulating implant 600 in a patient (sheep is shown).

In suitable embodiments, when compressed or under tension, the composites described herein generate a current density of between about 1 to about 250 microamps/mm$^2$. More suitably the composites generate a current density between about 1 to about 1000 microamps/mm$^2$, about 1 to about 150 microamps/mm$^2$, about 1 to about 100 microamps/mm$^2$, about 1 to about 90 microamps/mm$^2$, about 1 to about 80 microamps/mm$^2$, about 1 to about 70 microamps/mm$^2$, about 1 to about 60 microamps/mm$^2$, about 1 to about 50 microamps/mm$^2$, about 1 to about 30 microamps/mm$^2$, about 10 microamps/mm$^2$, about 20 microamps/mm$^2$, about 30 microamps/mm$^2$, about 40 microamps/mm$^2$, about 50 microamps/mm$^2$, about 60 microamps/mm$^2$, about 70 microamps/mm$^2$, about 80 microamps/mm$^2$, about 90 microamps/mm$^2$, or about 100 microamps/mm$^2$. Suitably, the current density supplied to the negative electrode 606 is either zero or a set level of direct current density as dictated by the power generated by the piezoelectric composite and the level set by the power converter.

This current density is ideally provided to increase tissue healing, e.g., the rate of bone fusion. As the piezoelectric composites described herein generate current density simply in response to pressure, no additional power source is required.

In embodiments, the tissue-stimulating composites described herein are strain coupled to bone or other body tissue so as to generate charge as the tissue undergoes strain, and the generated charge is applied via electrodes to a region where it is desired to stimulate a tissue, e.g., bone growth (see, e.g., U.S. Pat. No. 6,143,035, the entire disclosure of which is incorporated by reference herein in its entirety for all purposes). In embodiments, the composites described herein can be attached by pins or bone screws to a bone and the poles of the piezoelectric element are connected via leads to the power converter to carry the charge remotely and convert the charge to direct current to the electrode to promote healing.

In further embodiments, provided herein are methods of providing an electrical stimulation to a tissue of a patient, including a bone and in embodiments the spine of a patient. The methods suitably comprise implanting into the patient a tissue-stimulating implant as described herein. For example, the tissue-stimulating implant includes a piezoelectric composite, the piezoelectric composite comprising two or more layers, each layer comprising a polymer matrix, and a plurality of piezoelectric structures mechanically associated with the polymer matrix. As described herein, the layers are substantially adjacent to each other in a stacked configuration. The tissue-stimulating implant further includes an electrical connection connecting at least two of the layers of the piezoelectric composite, an electrically insulating encapsulation coating surrounding an exterior of the piezoelectric composite, and a power converter electrically connected to the piezoelectric composite and electrically connected to, or placed adjacent to, the tissue of the patient.

The methods further include placing the tissue-stimulating implant under a mechanical load, and providing a pulsed output voltage to the tissue of the patient. As described herein, it is believed that providing a pulsed output voltage, as compared to a constant voltage, aids in healing of patient tissues, including bone.

Exemplary ranges for the pulsed output voltage and timing of the pulses are described herein, and include for example, a pulsed output voltage at an average voltage of about 0.1 V to about 10 V, with a pulse width on the order of about 10-100 microseconds. In embodiments, the piezoelectric composite generates a current density of between about 1 microamps/mm$^2$ to about 50 microamps/mm$^2$, though additional current densities, as described herein, can also be generated.

EXAMPLES

Preparation of Stacked Piezoelectric Composite
Specimen Fabrication

Piezoelectric 1-3 composites were constructed using 800 μm diameter PZT 5A fibers (Smart Materials Corp., Sarasota, Fla.) in a medical grade epoxy (EPO-TEK 301, Epoxy Technology Inc., Billerica, Mass.) matrix. EPO-TEK 301 was chosen as the matrix material for both its handling characteristics and material properties. It is a room temperature cure two part thermoset epoxy, which makes it easy to work with. EPO-TEK 301 also has a compressive modulus and strength comparable to PEEK and good electrical properties. The piezoelectric fiber material, PZT 5A1, was chosen because of the favorable piezoelectric charge coefficient (440 C/N). Piezoelectric columns were constructed with a cross sectional surface area of 81 mm$^2$, a height of 100 mm. Composites contained a PZT fiber volume fraction of 30%. The composites were then sectioned to create layers of piezoelectric composite with an overall geometry based on an implant shape used in goat lumbar fusion studies.

The composites were sectioned into layers using a diamond blade saw into 1-mm, 1.5-mm, 3-mm, and 9-mm slices to assemble stacked piezoelectric composites with 9 layers (n=5), 6 layers (n=3), 3 layers (n=5), and 1 layer (n=6), respectively. The overall thickness of the stacked composite was 9 mm. Individual layers were sputter coated with a 100 nm thick layer of gold on top and bottom to ensure electrical connectivity between all fibers in each layer. Individual layers were then stacked and wired as shown in FIG. 3B, such that they were connected electrically in parallel but mechanically in series. Electrical connections were made using conductive adhesive-back copper tape and EPO-TEK 301 was used to mechanically bond layers together. All epoxy was allowed to cure at room temperature for at least 24 hours prior to poling. Finished implants can be seen in FIGS. 4A-4F.

Electromechanical Testing

Each composite was tested using two different procedures. Before testing, each composite was poled according to manufacturer's recommendations (1-2 kV/mm for 30-15 minutes). The first test procedure measured the voltage output of each composite across a sweep of 38 load resistances ranging from 420 kΩ to 5 GΩ under a compressive 1200 N preload with peak-to-peak compressive load amplitudes of 100, 500, and 1000 N and at loading frequencies of 1, 2, 3, and 5 Hz. The load amplitudes were chosen to be representative of loads expected in the intervertebral space after a spinal fusion surgery with instrumentation. Loading frequencies were representative of the range of normal human motion. The second testing procedure measured the voltage output of each sample at load resistances of 5.11 kΩ, 9.94 kΩ, 94.06 kΩ, and 16.76 MΩ with compressive preloads of 200, 400, 600, 800, 1000, and 1200 N (with a load amplitude of 100 N) and a constant loading frequency of 2 Hz. The average resistivity of cortical bone is about 1.55 kΩ-cm and the average specific capacitance is about 33.81 pF/cm when measured at 100 kHz. The load resistances of 5.11 kΩ, 9.94 kΩ, and 94.06 kΩ were chosen to be similar to tissue resistances. A loading frequency of 2 Hz was chosen as a normal gait frequency (1 Hz for each footstrike). Fifteen mechanical loading cycles were collected with a sampling rate of 512 Hz for all force amplitudes, frequencies, and load resistances using an MTS MiniBionix 858 (MTS Corp., Eden Prairie, Minn.) using a 2.5 kN load cell.

After collection, voltages were analyzed using a custom MATLAB computer code (Mathworks, Natick, Mass.). The first and last 2 cycles were removed, in order to analyze the steady state behavior of the device. Average maximum voltage was then calculated by taking the average of the voltage maxima during each loading cycle. The average maximum voltages were used to determine the average maximum power across the load resistances using Joule's Law ($P=V^2/R$). The statistical evaluation of all results was performed in MATLAB. Evaluation of the statistical significance of comparisons of the effects of preload, frequency, load amplitude, and poling procedure were done using matched pair t-tests with a significance level of 0.05. Evaluation of the statistical significance of comparisons of the effects of the number of layers in the specimen was done using unequal variance, two sample t-tests with a significance level of 0.05. Power analysis of data was performed post hoc using the sampsizepwr function in MATLAB. The sample mean was used for the mean under the alternative hypothesis.

Results

The effects of preload, load amplitude, frequency, and number of layers on power over a range of load resistances were measured. 83.5% of the comparisons had a power of 0.9 or greater and 90.6% of the comparisons had a power of 0.8 or greater.

As expected, varying preload did not significantly change the average maximum power produced by the composites ($p<0.05$). However, as anticipated, increasing load amplitude resulted in significant increases in average maximum power generation ($p<0.05$). The effects of load amplitude on average maximum power output of a 9 layer composite at 1200 N preload and 2 Hz are shown below in Table 3.

TABLE 3

Comparison of the Effects of Load Amplitude

| Load Amplitude (N) | Average Maximum Power (µW) |
|---|---|
| 100 | 8 |
| 500 | 261 |
| 1000 | 1190 |

Figure 8:
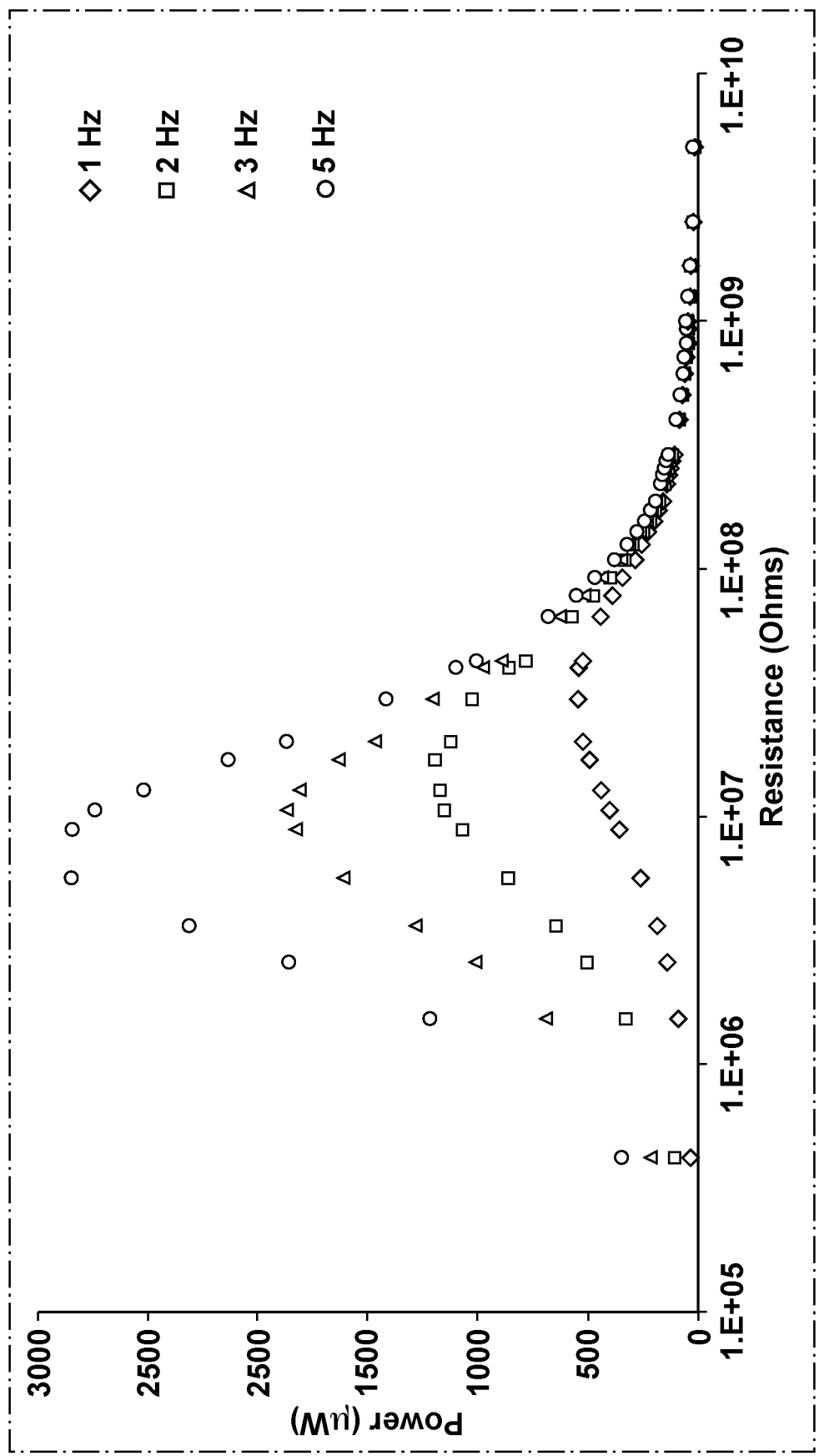
FIG. 8 shows the effect of frequency on power output of an exemplary stacked piezoelectric composite of an embodiment described herein.

FIG. 8 shows the relationship of power across load resistances for the 9 layer composite tested at 1000 N load amplitude at 1, 2, 3 and 5 Hz. Increases in frequency increased the peak power produced while significantly lowering the optimal load resistance of the generator ($p<0.05$).

Figure 9:
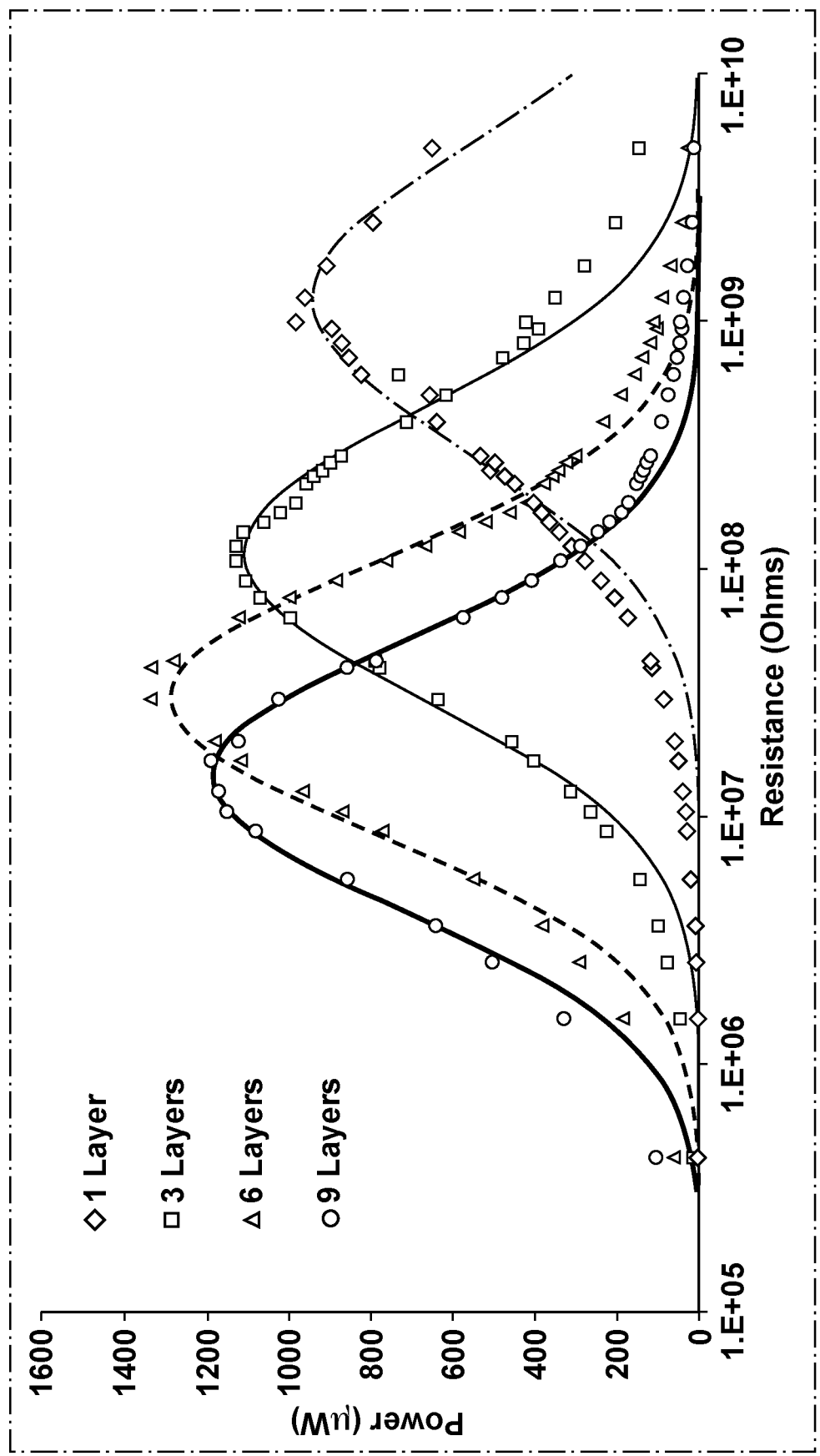
FIG. 9 shows the effect of varying the number of layers on power output of exemplary stacked piezoelectric composites of an embodiment described herein.

FIG. 9 shows average data from testing the 1, 3, 6 and 9-layer composites with the same overall volume fraction of piezoelectric fibers, at 2 Hz, 1000 N load amplitude, and 1200 N preload. Average maximum power obtained and optimal load resistance with respect to the number of layers in the composite is shown in Table 4.

TABLE 4

Average Maximum Power and Load Resistance

| Number of Layers | Average Maximum Power (µW) | Load Resistance (MΩ) |
|---|---|---|
| 1 | 984 ± 314 | 1000 |
| 3 | 1130 ± 452 | 108 |
| 6 | 1335 ± 475 | 30 |
| 9 | 1189 ± 439 | 17 |

Figure 10:
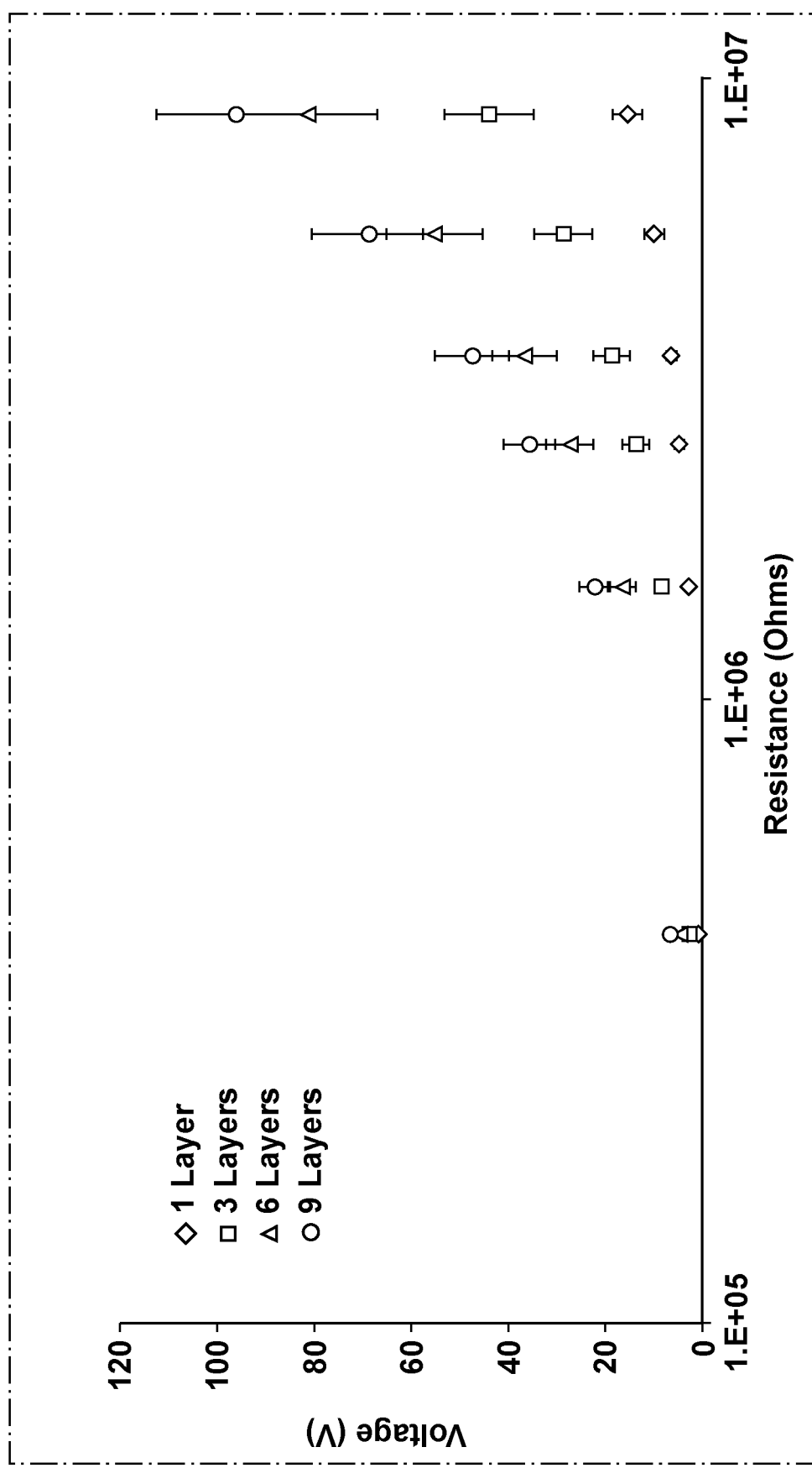
FIG. 10 shows the effect of varying the number of layers on voltage generated by a stacked piezoelectric composite of an embodiment described herein.

Load resistance significantly decreased with an increase in the number of layers ($p<0.05$). However, as predicted by a computational model, maximum power was not significantly influenced by the number of layers. FIG. 10 shows a nonlinear relationship of voltage output over a lower range of load resistances. An increase in the number of layers of the composites resulted in significantly higher voltage levels for a given load resistance ($p<0.05$).

DISCUSSION

The results of average peak power comparisons between composites with different numbers of layers show that the optimal load resistance was decreased from 1.00 GS to 16.78 MS as the number of layers was increased from one to nine, in close agreement with theoretical predictions. The average peak power generated from all of the composites at 1200 N preload, 1000 N load amplitude, and 2 Hz, was approximately 1132 W. The power generated by the composites is in excess of the power needed to directly produce the current density seen in current electrical stimulation devices. However, clinically used DC electrical stimulation devices are able to deliver a constant electronegative stimulation without rectification. In order to utilize the exemplified composites to generate DC electric stimulation, the power converter described herein is utilized.

DC Stimulation for Spinal Fusion—Animal Study

Methods

Five year old sheep used were used for the study. A tissue-stimulating implant as described herein (see FIG. 6) was utilized, along with two control, electrically active implants having the same shape and configuration. An active implant current density 10 µA/mm² was utilized. The devices were implanted in alternating locations in two skeletally mature sheep. Surgery was carried out by veterinarian and animal care at experienced CRO (Medtronic Physiological Research Laboratories). Non-load bearing buttress plates connected to only one vertebrae to keep implant from dislodging were utilized. After six weeks, computed tomography (CT) scans were taken. At 4 months, CT scans, histology and biomechanical testing were carried out.

Results

The electrically active implants showed more bone formation at both six weeks and four months.

At six weeks, CT scans showed that both active implants had full Grade 3 fusion while the controls were not fused at Grade 1.

Four month CT scans also showed Grade 3 fusion in the electrically active implants with no bone growth into the spinal canal. There was complete bone bridging in the active implants.

From histological analysis, both animals showed greater new bone formation in the active implant as compared to the control with no pathologic bone formation.

The intracagebone within both control specimens still had a narrow space of soft tissue precluding the bridging of the adjacent vertebral bodies.

Periosteal bone appeared to be denser in active specimens than in control and bone growth along the cage border (bone integration) was more intense in the active specimens than in the control Biomechanical testing confirmed the CT and histology findings. At four months, active implants showed lower range of motion and higher stiffness, indicating greater bone formation than in control implants.

It will be readily apparent to one of ordinary skill in the relevant arts that other suitable modifications and adaptations to the methods and applications described herein can be made without departing from the scope of any of the embodiments.

It is to be understood that while certain embodiments have been illustrated and described herein, the claims are not to be limited to the specific forms or arrangement of parts described and shown. In the specification, there have been disclosed illustrative embodiments, and although specific terms are employed, they are used in a generic and descriptive sense only and not for purposes of limitation. Modifications and variations of the embodiments are possible in light of the above teachings. It is therefore to be understood that the embodiments may be practiced otherwise than as specifically described.

What is claimed is:

1. A method of providing an electrical stimulation to a tissue of a patient, comprising:
    a. implanting into the patient a tissue-stimulating implant, the implant comprising:
        i. a piezoelectric composite, the piezoelectric composite comprising two or more layers, each of the two or more layers comprising:
            1. a polymer matrix;
            2. a plurality of piezoelectric structures mechanically associated with the polymer matrix, wherein the two or more layers are arranged in a stacked configuration; and
            3. an electrical connection connecting at least two of the two or more layers of the piezoelectric composite;
        ii. an electrically insulating encapsulation coating surrounding an exterior of the piezoelectric composite; and
        iii. a power converter electrically connected to the piezoelectric composite and electrically connected to, or adjacent to, the tissue of the patient,
    b. placing the tissue-stimulating implant under a mechanical load;
    c. transmitting electrical energy generated by the piezoelectric composite to the power converter; and
    d. providing, from the power converter, a pulsed output voltage to the tissue of the patient.

2. The method of claim 1, wherein the pulsed output voltage is at an average voltage of about 0.1 V to about 10 V.

3. The method of claim 1, wherein the pulsed output voltage has a pulse width on the order of about 10-100 microseconds.

4. The method of claim 1, wherein the piezoelectric composite comprises at least 2 layers, and wherein the 2 layers are connected mechanically in series and electrically in parallel.

5. The method of claim 1, wherein the piezoelectric composite generates a current density of between about 0.1 microamps/mm$^2$ to about 50 microamps/mm$^2$.

6. The method of claim 1, wherein the power converter is connected to, or adjacent to, a bone of the patient.

7. The method of claim 1, wherein the pulsed output voltage has a pulse width less than 100 microseconds.

8. The method of claim 7, wherein the pulse width ranges from 50 microseconds to 100 microseconds.

9. The method of claim 7, wherein the pulse width ranges from 70 microseconds to 90 microseconds.

10. The method of claim 9, wherein the providing, from the power converter, the pulsed output voltage, further comprises:
    determining that a charge in the at least one capacitor has reached a predetermined voltage threshold; and
    discharging the at least one capacitor to generate the pulsed output voltage.

11. The method of claim 1, wherein the providing, from the power converter, the pulsed output voltage, comprises:
    charging at least one capacitor in the power converter with the electrical energy transmitted by the piezoelectric composite.

12. The method of claim 11, wherein the predetermined voltage threshold ranges from 4 volts to 5 volts.

* * * * *